(12) United States Patent
Gu et al.

(10) Patent No.: US 9,395,353 B2
(45) Date of Patent: Jul. 19, 2016

(54) NANOPORE-FACILITATED SINGLE MOLECULE DETECTION OF NUCLEIC ACID

(75) Inventors: Li-Qun Gu, Columbia, MO (US); Yong Wang, Columbia, MO (US); Kai Tian, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 791 days.

(21) Appl. No.: 13/810,105

(22) PCT Filed: Jul. 14, 2011

(86) PCT No.: PCT/US2011/044082
§ 371 (c)(1),
(2), (4) Date: May 14, 2013

(87) PCT Pub. No.: WO2012/009578
PCT Pub. Date: Jan. 19, 2012

(65) Prior Publication Data
US 2013/0220809 A1     Aug. 29, 2013

Related U.S. Application Data

(60) Provisional application No. 61/399,578, filed on Jul. 14, 2010.

(51) Int. Cl.
*G01N 27/327* (2006.01)
*G01N 33/487* (2006.01)
*C12Q 1/68* (2006.01)

(52) U.S. Cl.
CPC ........ *G01N 33/48721* (2013.01); *C12Q 1/6825* (2013.01)

(58) Field of Classification Search
CPC .............................................. G01N 33/48721
See application file for complete search history.

(56) References Cited

U.S. PATENT DOCUMENTS

| 6,362,002 B1 | 3/2002 | Denison et al. |
| 6,428,959 B1 | 8/2002 | Deamer |

(Continued)

FOREIGN PATENT DOCUMENTS

| WO | 01/42782 A1 | 6/2001 |
| WO | 03/000920 A2 | 1/2003 |

(Continued)

OTHER PUBLICATIONS

Maglia et al., Enhanced translocation of single DNA molecules through α-hemolysin nanopores by manipulation of internal charge, PNAS Dec. 16, 2008, vol. 105, No. 50, pp. 19720-19725.*

(Continued)

*Primary Examiner* — Alexander Noguerola
(74) *Attorney, Agent, or Firm* — Thompson Coburn LLP; Charles P. Romano

(57) ABSTRACT

The present invention provides a new and improved oligonucleotide detection method based on the nanopore technology with a probe containing a complementary sequence to the target oligonucleotide and a terminal extension at the probe's 3' terminus, 5' terminus, or both termini. The improved nanopore sensor with the probe enables sensitive, selective, and direct detection, differentiation and quantification of target oligonucleotides such as miRNAs. The inventive detection method may also be employed as a non-invasive and cost-effective diagnostic method for cancer detection based on miRNA levels in the patient's blood sample.

29 Claims, 20 Drawing Sheets

(56) References Cited

U.S. PATENT DOCUMENTS

| | | | |
|---|---|---|---|
| 2002/0137089 | A1 | 9/2002 | Deamer |
| 2003/0044816 | A1 | 3/2003 | Denison et al. |
| 2005/0019784 | A1 | 1/2005 | Su et al. |
| 2005/0131211 | A1 | 6/2005 | Bayley et al. |
| 2005/0136408 | A1 | 6/2005 | Tom-Moy et al. |
| 2005/0208574 | A1 | 9/2005 | Bayley et al. |
| 2006/0003458 | A1 | 1/2006 | Golovchenko et al. |
| 2006/0183112 | A1 | 8/2006 | Min et al. |
| 2006/0292605 | A1 | 12/2006 | Kim et al. |
| 2007/0190542 | A1 | 8/2007 | Ling et al. |
| 2007/0190543 | A1 | 8/2007 | Livak |
| 2007/0218471 | A1 | 9/2007 | Kim et al. |
| 2008/0182239 | A1 | 7/2008 | Mullinax et al. |
| 2009/0029477 | A1 | 1/2009 | Meller et al. |
| 2009/0136958 | A1 | 5/2009 | Gershow et al. |
| 2009/0181390 | A1 | 7/2009 | Li et al. |
| 2009/0274870 | A1 | 11/2009 | Harnack et al. |
| 2009/0286969 | A1 | 11/2009 | Esau et al. |
| 2010/0035260 | A1 | 2/2010 | Olasagasti et al. |
| 2010/0099198 | A1 | 4/2010 | Zhao et al. |
| 2010/0148126 | A1 | 6/2010 | Guan et al. |
| 2010/0291548 | A1 | 11/2010 | Sharaf et al. |
| 2011/0003703 | A1 | 1/2011 | Ma et al. |
| 2011/0028334 | A1 | 2/2011 | Hayden |
| 2011/0053284 | A1 | 3/2011 | Meller et al. |
| 2011/0193570 | A1 | 8/2011 | Chen et al. |

FOREIGN PATENT DOCUMENTS

| | | |
|---|---|---|
| WO | 03/067210 A2 | 8/2003 |
| WO | 2007/041621 A2 | 4/2007 |
| WO | 2008/097190 A1 | 8/2008 |
| WO | 2009/007743 A1 | 1/2009 |
| WO | 2009/020682 A2 | 2/2009 |
| WO | 2009/092035 A2 | 7/2009 |
| WO | 2010/004273 A1 | 1/2010 |
| WO | 2011/028494 A2 | 3/2011 |
| WO | 2011/103424 A2 | 8/2011 |
| WO | 2011/126869 A2 | 10/2011 |
| WO | 2012/009578 A2 | 1/2012 |
| WO | 2012/083249 A2 | 6/2012 |
| WO | 2013121201 A1 | 8/2013 |

OTHER PUBLICATIONS

Wang, et al., "Nanopore-Based Detection of Circulating microRNAs in Lung Cancer Patients", Nature Nanotechnology, Apr. 1, 2012, pp. 668-674, vol. 6, No. 10.

Borsenberger et al., "Chemically Labeled Nucleotides and Oligonucleotides Encode DNA for Sensing with Nanopores", Journal of the American Chemists Society, 2009, pp. 7530-7531, vol. 31.

Kumar et al., "PEG-Labeled Nucleotides and Nanopore Detection for Single Molecule DNA Sequencing by Synthesis", Scientific Reports, 2012, pp. 684, vol. 2.

Livnah et al., "Three-Dimensional Structures of Avidin and the Avidin-Biotin Complex", Proceedings of the National Acadamy for the Sciences, USA, Jun. 1993, pp. 5076-5080, vol. 90.

Ma et al., "Biological Nanopores for Single-Molecule Biophysics", ChemBioChem, Jan. 4, 2010, pp. 25-34, vol. 11 No. 1.

Nakane et al., "A Nanosensor for Transmembrane Capture and Identification of Single Nucleic Acid Molecules" Biophysical Journal, Jul. 1, 2004, pp. 615-621, vol. 87 No. 1.

Soni et al., Progress Toward Ultrafast DNA Sequencing Using Solid-State Nanopores, Clinical Chemistry, Nov. 1, 2007, pp. 1996-2001, vol. 53 No. 11.

Wang et al., "In 3108-Pos A Novel Molecular Signature for Discriminating DNA Unzipping in a Nanopore", Biophysical Journal, Jan. 23, 2010, pp. 599A-699A, No. 98, No. 3, Retrieved from the Internet: URL: http://www.sciencedirect.com/science/article/pii/S00063495 09050681/pdfft?md5=150abaa4a8a7556592b390e3ca90b724&pid=1-s2.0-S0006349509050681-main.pdf [retrieved on Jan. 17, 2014].

Aksimentiev et al., "Imaging alpha-Hemolysin with Molecular Dynamics: Ionic Conductance, Osmotic Permeability, and the Electrostatic Potential Map", Biophysical Journal, 2005, pp. 3745-3761, vol. 88.

Bhattacharya et al., Rectification of the Current in alpha-Hemolysin Pore Depends on the Cation Type: The Alkali Series Probed by Molecular Dynamics Simulations and Experiments, The Journal of Physical Chemistry, 2011, pp. 4255-4264, vol. 115.

Fan et al., "Detection of MicroRNAs Using Target-Guided Formation of Conducting Polymer Nanowires in Nanogaps", Journal of the American Chemical Society, 2007, pp. 5437-5443, vol. 129, No. 7.

Kim et al., "Detecting Translocation of Individual Single Stranded DNA Homopolymers Through a Fabricated Nanopore Chip", Frontiers in Bioscience, 2007, pp. 2978-2983, vol. 12.

Luan et al., "Electric and Electrophoretic Inversion of the DNA Charge in Multivalent Electrolytes", The Royal Society of Chemistry/Soft Matter, 2010. pp. 243-246, vol. 6.

Purnell et al., "Discrimination of Single Base Substitutions in a DNA Strand Immobilized in a Biological Nanopore", ACS Nano, 2009, pp. 2533-2538, vol. 3, No. 9.

Skinner et al., "Distinguishing Single- and Double-Stranded Nucleic Acid Molecules Using Solid-State Nanopores", Nano Letters, 2009, pp. 2953-2960, vol. 9, No. 8.

Wanunu et al., "Rapid Electronic Detection of Probe-Specific MicroRNAs Using Thin Nanopore Sensors", Nature Nanotechnology, 2010, pp. 807-814, vol. 5.

Astier et al., "Toward Single Molecular DNA Sequencing: Direct Identification of Ribonucleoside and Deoxyribonucleoside 5'-Monophosphates by Using an Engineered Protein Nanopore Equipped with a Molecular Adapter", Journal of the American Chemical Society, 2006, pp. 1705-1710, vol. 128, No. 5.

Bond et al., "Molecular Dynamics Simulations of DNA within a Nanopore: Arginine-Phosphate Tethering and a Binding/Sliding Mechanism for Translocation", Biochemistry, 2011, pp. 3777-3783, vol. 50.

Butler et al., "Single-molcule DNA detection with an engineered MspA protein nanopore", Proceedings of the National Academy of Science, Dec. 30, 2008, pp. 20647-20652, vol. 105, No. 52.

Gao et al., "A simple method of creating a nanopore-terminated probe for single-molecule enantiomer discrimination", Analytical Chemistry, Jan. 1, 2009, pp. 80-86, vol./No. 81(1).

Howorka et al., "Sequence-specific detection of individual DNA strands using engineered nanopores", Nature Biotechnology, Jul. 2001, pp. 636-639, vol. 19.

Mitchell et al., "Chemical Tags Facilitate the Sensing of Individual DNA Strands with Nanopores", Angewandte Chemie, 2008, pp. 5565-5568.

Purnell et al., "Nucleotide Identification and Orientation Discrimination of DNA Homopolymers Immobilized in a Protein Nanopore", Nano Letters, 2008, pp. 3029-3034, vol. 8, No. 9.

Singer et al., "Nanopore-based Sensing of Individual Nucleic Acid Complexes", Israel Journal of Chemistry, 2009, pp. 323-331, vol. 49.

Singer et al., "Nanopore Based Sequence Specific Detection of Duplex DNA for Genomic Profiling", Nano Letters, 2010, pp. 738-742, vol. 10.

Thomson et al., "Preliminary nanopore cheminformatics analysis of aptamer-target binding strength", BMC Bioinformatics, 2007, 13 pages, vol. 8(Suppl 7).

Winters-Hilt, "Nanopore Detector based analysis of single-molecule conformational kinetics and binding interactions", BMC Bioinformatics, 2006, 27 pages, vol. 7(Supple 2).

Tian et al., "Designing a Polycationic Probe for Simultaneous Enrichment and Detection of MicroRNAs in a Nanopore", ACS NANO, 2013, pp. 3962-3969, vol. 7 No. 5.

\* cited by examiner

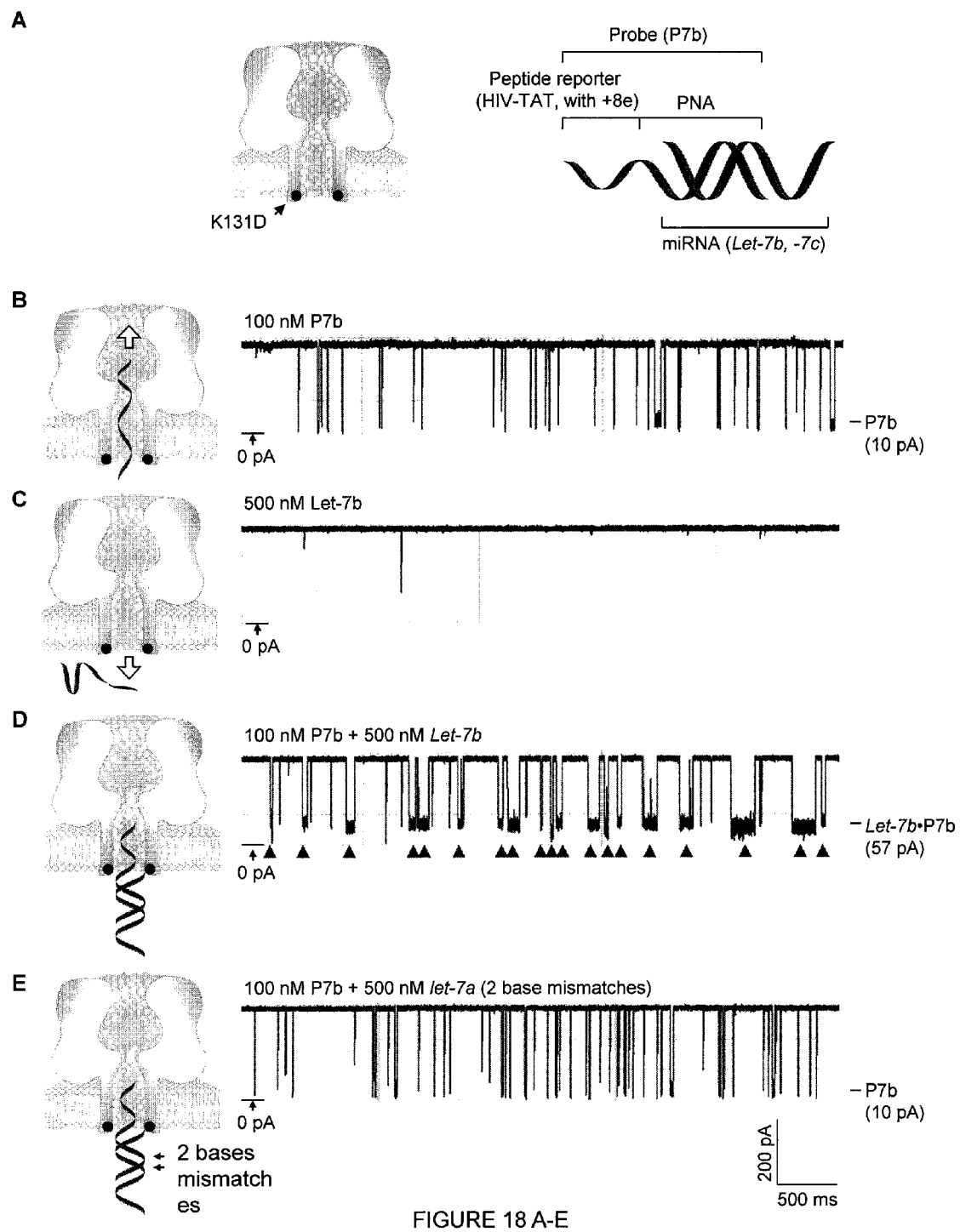
FIGURE 18 A-E

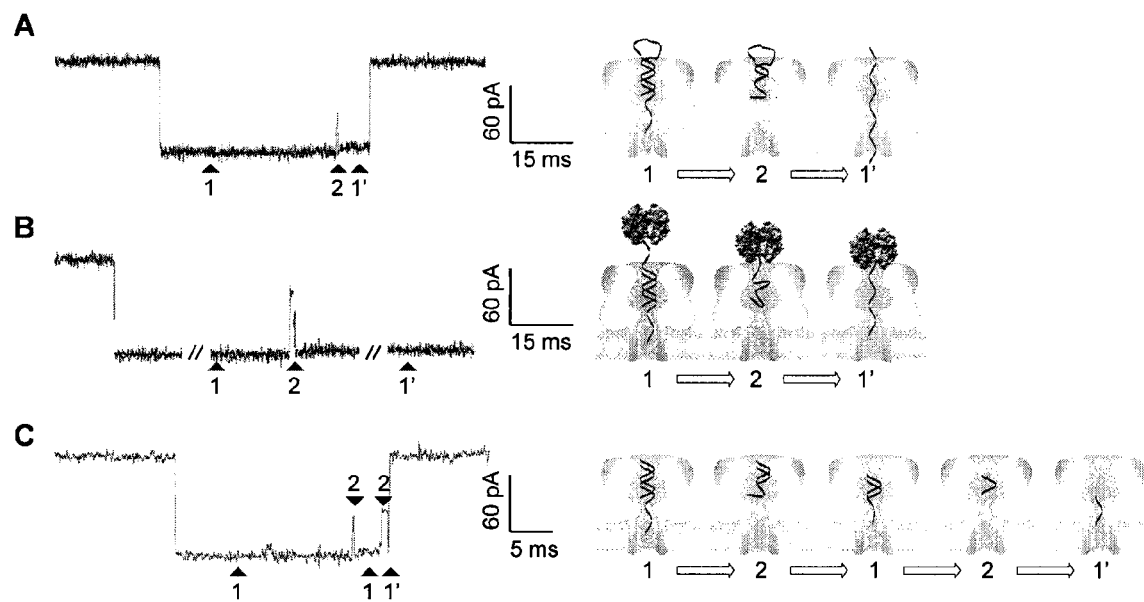
FIGURE 19 A-C

NANOPORE-FACILITATED SINGLE MOLECULE DETECTION OF NUCLEIC ACID

RELATED APPLICATIONS

This application is a National Stage application of International Patent Application No PCT/US2011/044082, filed Jul. 14, 2011, which is incorporated herein by reference in its entirety and which claims the benefit of U.S. Provisional Patent Application No. 61/399,578, filed Jul. 14, 2010, which is incorporated herein by reference in its entirety.

GRANT STATEMENT

This invention was made with government support under Grant No. GM079613 awarded by the National Institute for Health. The government has certain rights in the invention.

FIELD OF INVENTION

This product relates to a method/apparatus of single-molecule detection, more specifically, to a method/system for quantitative detection of single strand nucleic acids, such as microRNAs, employing an ultrasensitive, low noise nanopore-based single-molecule technology.

SEQUENCE LISTING STATEMENT

The sequence listing that is contained in the file named "52553_110702_ST25.txt ", which is 12,350 bytes in size (measured in operating system MS-Windows), created on Jan. 14, 2013, is filed herewith by electronic submission and incorporated herein by reference in its entirety.

BACKGROUND OF INVENTION

MicroRNAs.

MicroRNAs (miRNAs) are a class of short (~18-24 nucleotides) noncoding RNAs that regulate gene expression at the post-transcriptional level[2]. Depending on the degree of homology to their target sequences, miRNA binding induces either translational repression or cleavage of target mRNAs[2]. As powerful gene regulators, miRNAs play important roles in development, cell differentiation, and regulation of cell cycle, apoptosis and signaling pathways[2,3]. Aberrant expression of miRNAs has been found in all types of tumors[4,5]; the different cancer types have distinct miRNA expression profiles[6]. Specific miRNAs including some miRNA families containing a few nucleotide differences are constantly released from the primary tumor into blood stream and present in an incredible stable form[7]. Recent studies demonstrated that circulating miRNAs are enveloped inside exosomal vesicles and can be transferable and functional in the recipient cells[8,9]. Thus, detection of tumor specific circulating miRNAs provides a powerful tool for early diagnosis, staging, and monitoring of cancer cells[10].

MiRNA Detection.

Several technologies including reverse transcription real-time PCR (RT-qPCR) and microarray for miRNA detection have been developed[11-13]. Each technology has its own advantages, but limitations include requiring enzymatic amplification and semi-quantitative results[14]. In particular the short miRNA sequences make it difficult to selectively design the primers or probes, resulting in cross-hybridization and low selectivity. This is especially true when the miRNAs contain a few or a single nucleotide difference in a miRNA family. Emerging techniques based on colorimetry, biolumi- nescence, enzyme turnovers and electrochemistry have been proposed, and nanoparticles and molecular beacon have been applied to miRNA detection with high sensitivity and selectivity (review[14]). But the intrinsic versatility needs to be improved. Recently, the integration of single-molecule fluorescence and lock-nucleic acids (LNA)[15] probes provided a sensitive method for miRNA profiling in tissue samples[16], though this method requires expensive instrument.

Nanopore Single Molecule Detection.

In a nanometer-scaled pore structure, the ion current becomes very sensitive to the presence, location and conformation of single target molecules occupying the ion pathway[17]. This sensitivity allows "visualizing" single molecules, elucidating their kinetics from characteristic change in the pore conductance, and quantifying the target from the occurrence of single molecule signature events. Nanopores have been developed as receptive single molecule detectors for broad biotechnological applications (reviews[17-19]). The nanopore is also recognized as one of the next generations of DNA sequencing technologies[20,21]. For example, the 2-nm nanopore, α-hemolysin transmembrane protein pore, allows rapid translocation of single-stranded oligonucleotide, which has been well characterized for DNA sequencmg[22-27]. However, the molecular translocation-based sensing mode is not suitable for miRNA detection because the sequences of all mature miRNAs are short (18-24 nt), and when traversing the nanopore, the current signals by different miRNAs are indistinguishable.

Therefore, there is a need to provide a new miRNA detection method based on nano-scale pore structure with improved sensitivity, speedy process, and cost efficiency.

SUMMARY OF INVENTION

In one aspect of the invention, a new and improved nanopore-based sensing system for detection and differentiation of single strand oligonucleotides, such as miRNAs, is described. The inventive system for detecting a target single strand oligonucleotide comprises 1) a nanopore, 2) a power source providing sufficient voltage to induce unzipping, 3) a probe with its center domain complementary to the target oligonucleotide, whereas the unzipping of the hybrid of target oligonucleotide and the probe in the nanopore induces certain identifiable current signal changes, and 4) means for detecting the current signal changes. The inventive probe further comprises at least one signal tag at its 3' or 5' terminal (or both). The signal tag may be of any charged single chain molecule with sufficient length to assist the unzipping translocation through the nanopore driven by the voltage. For example, the signal tag may be oligonucleotides such as poly(dC)$_n$, poly(dA)$_n$, and poly(dT)$_n$, or charged polypeptides.

In another aspect of the invention, a new and improved method based on nanopore technology for detecting and differentiating single strand oligonucleotide is described. The inventive method detects the current changes triggered by the unzipping of the hybrid of the target oligonucleotide and its probe in a nanopore. The inventive method includes the step of 1) mixing the target oligonucleotide with a pre-designed probe, which has its central domain matching the target sequence and a charged single chain molecule tagged to at least one of its 3' and 5' terminals, to produce a sample mixture, 2) loading the mixture into the cis chamber of a nanopore system, and a voltage is added from the trans chamber, and 3) recording current output for a pre-determined time period.

In yet another aspect of the invention, a new and improved method for detecting and monitoring cancer-related miRNAs in patients' blood sample is described. The inventive method includes the steps of 1) mixing the total plasma RNAs extracted from a patient's blood sample with the miRNA probe that contains the complementary sequence to the targeting miRNA and a signal tag at the probe's 3'-terminal, 5'-terminal, or both, 2) adding the mixture into a nanopore chamber with a preselected voltage, and 3) monitoring and analyzing the signature events in the output current traces that serves as an electrical marker for single miRNA molecule recognition.

In certain embodiments, a probe molecule for detecting of a single strand oligonucleotide, such as miRNA, using a nanopore comprising: 1) a center domain with a complementary sequence to the target oligonucleotide, and 2) a terminal extension tagged to at least one of the center domain's 3' or 5' terminals is provided. In certain embodiments, the terminal extension is a charged chain molecule. In certain embodiments, the terminal extension is a charged polypeptide. In certain embodiments, terminal extension is a charged polymer.

In certain embodiments, the invention provides a method of detecting single strand oligonucleotide with a dual-compartment nanopore system, whereas the system includes a cis compartment and a trans compartment divided by a partition with an opening at its center region, recording solution filling both compartments and a lipid bilayer formed at the opening on the partition, a nanopore plugging through the lipid bilayer bridging the cis and trans chamber, a voltage loaded upon the system via a pair of electrodes each extruding from the cis or trans compartment, and a current detector monitoring the current changes, includes the steps of 1) mixing the target oligonucleotide with a pre-designed probe, which has its central domain matching the target sequence and a charged single chain molecule tagged to at least one of its 3' and 5' terminals, to produce a sample mixture, 2) loading the mixture into the cis compartment, 3) providing the system with a pre-determined voltage, and 4) recording current output for a pre-determined time period. In certain embodiments of the methods, the recording step can further comprise the step of analyzing the current change induced by the hybrid of the target oligonucleotide and the probe undergoes unzipping in the nanopore.

The instant invention also includes probes, nanopores, kits comprising the probes and nanopores, and associated methods of use described in the following portions of the specification, drawings, and claims provided herewith.

DESCRIPTION OF DRAWINGS

FIG. 4(A) is a current trace showing different types of blocks. The block profiles and corresponding molecular processes is depicted in panel B, C and D; FIG. 4(b)/(b') is an exemplary spike-like short block produced by free miR-155 or $P_{155}$ molecules translocating through the pore; FIG. 4(c)/(c') is an amplified long block with multiple conductance levels which are sequentially generated by unzipping of a miR-155·$P_{155}$ hybrid, confinement of miR-155 in the nanocavity and translocation of miR-155; FIG. 4(d)/(d') is an exemplary long blocks with a single conductance level, produced by a trapped mir-155·$P_{155}$ hybrid that exits from the cis entrance without unzipping.

FIG. 18 A-F shows: A) the diagram of the miRNA/probe complex. FIG. 18 B shows events for translocation of the peptide-PNA probe, P7b. The characteristic events last for 3 ms and reduce the current to 10 pA at +180 mV. FIG. 18C shows that no block events can be observed with free miRNA let-7b (without probe) in the solution at +180 mV. FIG. 18D shows signature events for the trapping of the let-7b/P7b complex. FIG. 18E shows that Let-7c, which has two different nucleotides from Let-7b, cannot bind to PNA of the probe P7b, therefore does not generate signature events as in FIG. A1c. Almost all observed events are due to the probe itself.

FIG. 19 A-C shows: FIG. 19A, when employing HP-C30 with a hairpin at the 3'-end of short strand, we observed a novel type of three-level current pattern. FIG. 19B, when using SA-C30 attached with a streptavidin at the 3'-end of the short strand, we also observed a new multi-level current pattern. FIG. 19C shows when using a short oligonucleotide to link two DNAs, the complex can be sequentially unzipped in the nanopore in two steps. The two unzipping can be clearly revealed by the two Level 2 states.

DETAILED DESCRIPTION OF INVENTION

The invention provides a robust nanopore sensing system that enables sensitive, selective and direct detection, differentiation and quantification of single strand oligonucleotide, such as miRNAs. Additionally, the inventive sensing technology can also be employed to discriminate single nucleotide differences in miRNA family members. Furthermore, the inventive technology has the potential for non-invasive and cost-effective early diagnosis and continuous monitoring of cancer markers in patients' blood samples.

The inventive nanopore sensing system for detecting a target single-strand oligonucleotide, such as a miRNA, includes 1) a nanopore allowing rapid translocation of single-stranded oligonucleotide, 2) a power source providing a pre-determined voltage as driving force to induce unzipping of a double-stranded oligonucleotide, 3) a probe molecule to be mixed with the target oligonucleotide and loaded into the nanopore, and the unzipping of the hybrid of target oligonucleotide and the probe in the pore produces certain identifiable current signal changes, and 4) a means for detecting current changes.

Figure 1:
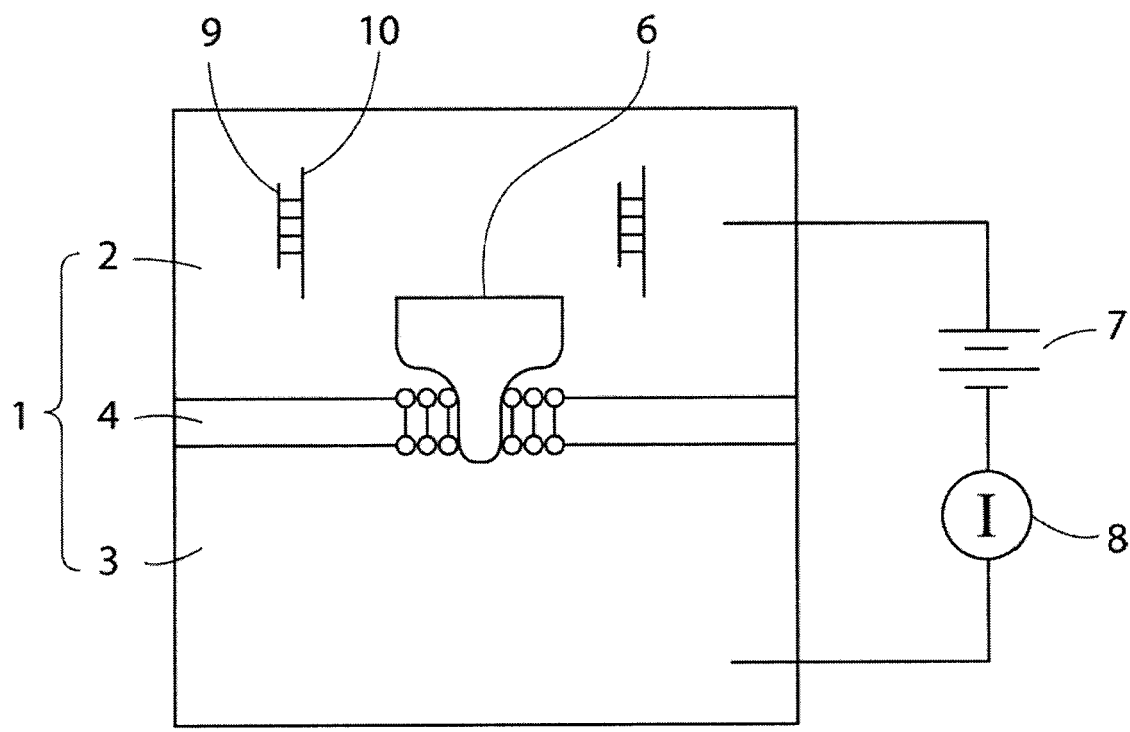
FIG. 1 is a schematic diagram of an exemplary nanopore sensing system, according to one embodiment of the invention.

Refer to FIG. 1, which is a schematic illustration of an exemplary nanopore sensing system. As shown in FIG. 1, the sensing chamber, 1, includes a cis compartment, 2, and a trans compartment, 3, which are divided by a partition, 4. Both compartments are filled with a pre-selected recording solution such as 1 M KCl. The partition, 4, has an opening, 5, in its center region, over which a lipid bilayer is formed, and the nanopore, 6, is plugged through the lipid bilayer. The power, 7, provides a voltage that is loaded through a pair of electrodes in the two compartments; the current detector, such as a pico-Ampere amplifier, 8, is connected to monitor the current changes. Upon the testing, a mixture sample of the target oligonucleotide, 9, and its complementary probe, 10, is loaded into the cis compartment, 2.

Figure 2:
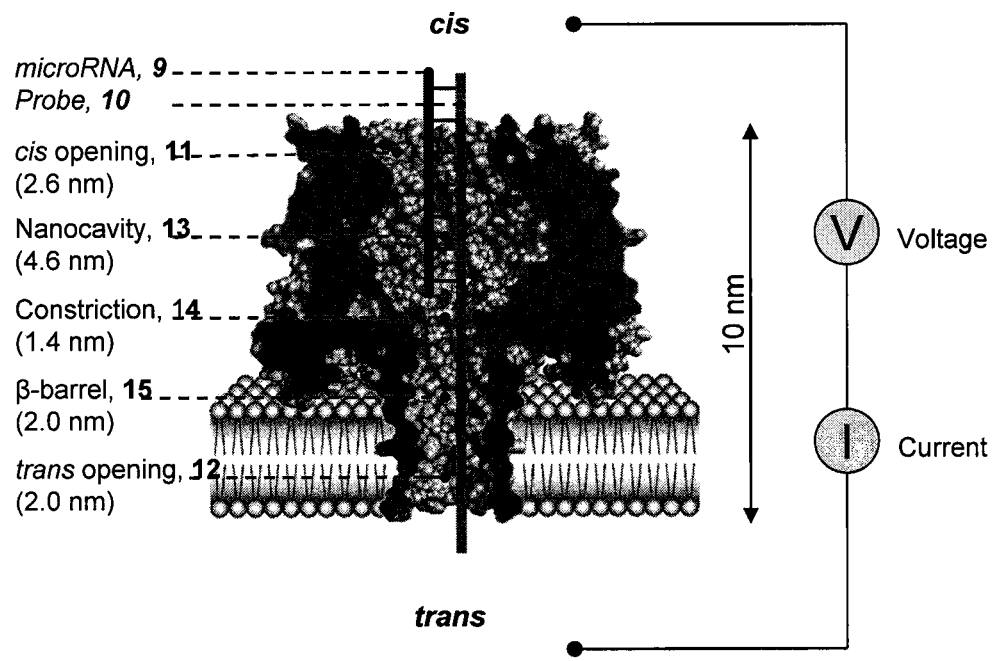
FIG. 2 is a schematic amplified illustration of an exemplary nanopore plugged through the lipid bilayer.

Refer to FIG. 2, which is a schematic amplified illustration of the nanopore, 6. As shown in FIG. 2, the nanopore, 6, is in conical or funnel shape with two openings, the cis opening, 11, at the wide end and the trans opening, 12, down the narrow end. During the detection, the paired oligonucleotides, 9/10, is captured into the nanocavity, 13. The voltage then drive the oligonucleotides, 9/10, to unzip at the constriction, 14, with the probe, 10, first traversing through the β-barrel, 15, and out off the trans opening, 12, and followed by the traversing of the target oligonucleotide, 9.

The nanopore may be any ion channel of cone-shape or any asymmetrical shape with a wide and a narrow opening plugged into the planar lipid bilayer that has a wider cavity followed by a narrow channel that can facilitate unzipping translocation events. The nanopore may be any existing protein ion channels, such as the α-hemolysin transmembrane protein pore adopted in the examples below, or various synthetic pores fabricated using fashion nanotechnologies with abiotic materials such as silicon.

The inventive probe is a multi-domain single strand molecule, which comprises a central domain fully complementary to the target oligonucleotide and at least one terminal extension, i.e., signal tag, at its 3' or 5' terminal, with signal tags at both terminals as preferred. The invention suggests the 3'-tagged probe is preferred over the 5'-tagged probe. The probe directionality-dependence of the capture rate is possibly due to that the bases of ssDNA tilt collectively toward the 5' end of the strand[38], and this asymmetric base orientation makes DNA move more easily from 3'-end than 5'-end.

The terminal extension (signal tag) may be of any charged single chain molecule with sufficient length to assist the unzipping translocation through the nanopore driven by the voltage. The signal tag may be a charged polymer chain, which can be an oligonucleotide such as $poly(dC)_n$, $poly(dA)_n$, and or $poly(dT)_n$, or a charged polypeptide. For example, when α-hemolysin transmembrane protein pore is employed as the nanopore, the poly(dC) tag is more preferred over poly(dA) or poly(dT) tags; furthermore, the $poly(dC)_{30}$ is much more efficient in generating signature events (discussed below) than that with a shorter tag such as $poly(dC)_8$. The capture rate can be further enhanced once combined with other effective approaches, including detection at high voltage, use of engineered pores with designed charge profile in the lumen[33], and detection in asymmetrical salt concentrations between both sides of the pore[39].

Figure 3:
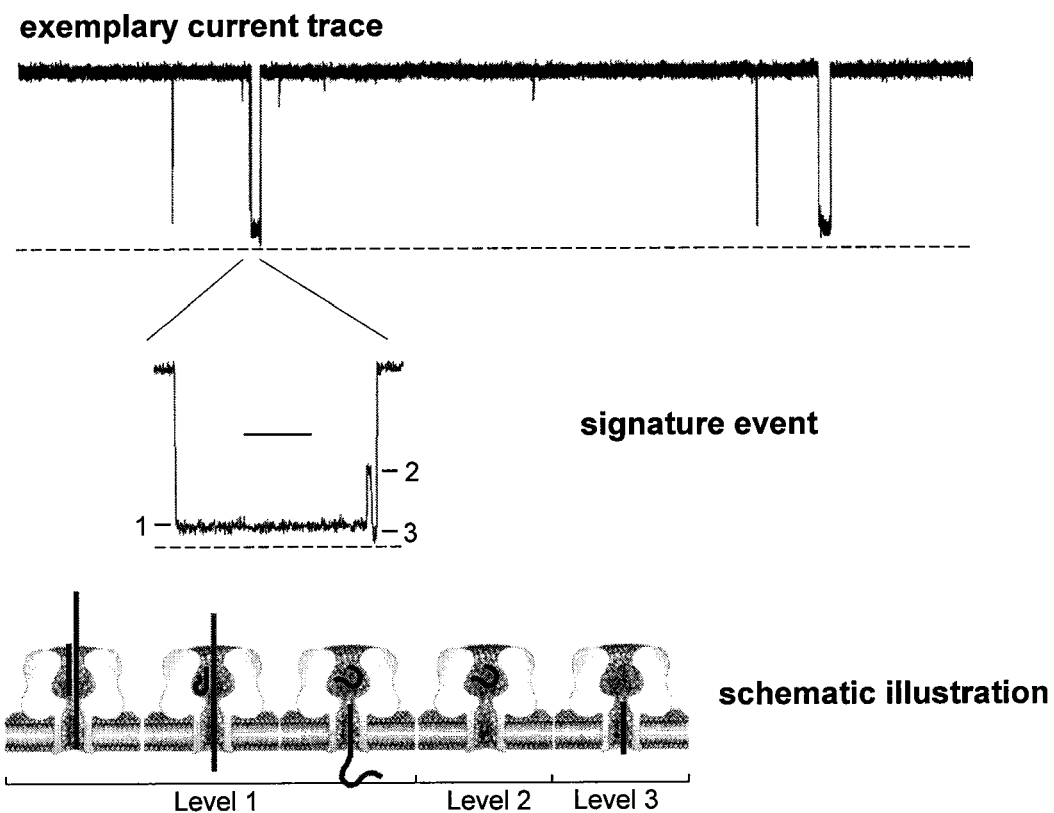
FIG. 3 includes an exemplary current trace, an amplified electrical mark of the signature event, and a schematic illustration of the unzipping and translocation event.

The invention also provides a method of detecting and differentiating single strand oligonucleotides by monitoring the current changes induced by the unzipping and translocation of the oligonucleotides through a nanopore. The inventive method of detecting single strand oligonucleotide with a dual-compartment nanopore system, as the one illustrated in FIG. 1, includes the steps of 1) mixing the target oligonucleotide with a pre-designed probe, which has its central domain matching the target sequence and a charged single chain molecule tagged to at least one of its 3' and 5' terminals, to produce a sample mixture, 2) loading the mixture into the cis compartment, 3) providing the system with a pre-determined voltage, and 4) recording current output for a pre-determined time period. The current change induced by the unzipping and translocation of the hybrid of the target oligonucleotide and its complementary probe through the nanopore is a unique signature event, which is used to detect and differentiate the target oligonucleotide. Refer to FIG. 3, which includes an exemplary current trace recorded during an exemplary detection, an amplified electrical mark of the signature event, and a schematic illustration of the unzipping-translocation event.
Further Description

DEFINITIONS

As used herein, the term "ROC curve" refers to a Receiver Operating Characteristic Curve. An ROC curve used to analyze the relationship between selectivity and sensitivity. An ROC curve separates the plot into up and lower regions.

As used herein, the term "AUC" refers to the Area under the ROC curve. An AUC can range between 0.5-1.0. The higher the AUC value, the better the separation result.

As used herein, the term "OCP" refers to an Optimized Cutoff Point. In certain embodiments, an OCP can be calculated from ROC curves. In certain embodiments, an OCP is a cutoff duration at the maximal value of a Youden index.

As used herein, the phrase "Youden index" is defined as {sensitivity+selectivity−1}. A Youden index is calculated from the ROC curve, and can range between 0 and 1. A cutoff duration leading to complete separation of long and short duration distribution results in Youden index=1, whereas complete overlap gives Youden index=0. In certain embodiments, a cutoff duration value that returns the maximum of Youden index, i.e. "optimal" cutoff point (OCP) (Greiner et al., 2000 Preventive Veterinary Medicine 45, 23-41) gives the most accurate separation.

Description of the Probes, Nanopores, Kits Comprising the Probes and Nanopores, and Associated Methods of Use In one broad aspect, the instant invention is directed to probes, nanopores, kits comprising the probes and nanopores, and associated methods of use, that provide for "signature" current blockage events that distinguish those events arising from interactions with the probe and target from other events. In this context, the other events are referred to as "background" events. Background events include, but are not limited to, interactions of a probe with nucleic acid that is not a target, interactions of a probe with other components present in a nanopore detection system, free nucleic acids present in the nanopore detection system, and the like. Such features of such signature events include, but are not limited to, at least one of a: i) a current block of different duration than a background current block; ii) a different number of distinct current blockade levels than a background current block; iii) a different order of occurrence of current blockade levels than a background current block; iv) a different current amplitude at a blockade level than a background current block; v) a different current amplitude of each blockade level than a background current block; or any combination of (i), (ii), (iii), (iv), or (v). In certain embodiments, a signature blockage event can be distinguished from a background blockage event by differences in a characteristic background noise of each blockage event. In certain embodiments, the distinct durations, numbers, or amplitude(s) in the signature event are greater than those observed in the background event. In certain embodiments, the distinct durations, numbers, or amplitude(s) in the signature event are less than those observed in the background event. In certain embodiments, the distinct durations, numbers, orders, or amplitude(s) in a signature event are statistically distinguishable from those of a background event. In certain embodiments, the signature events are provided in nanopore systems comprising a protein nanopore formed by alpha-hemolysin (αHL) or engineered variants thereof in a planar lipid bilayer system. In certain embodiments, the signature events can be provided in a biochip formed by hydrogel-encapsulated lipid bilayer with a single protein nanopore embedded therein or a micro-droplet bilayer system. Biochips and micro-droplet bilayer systems have been described (Shim and Gu; Stochastic Sensing on a Modular Chip Containing a Single-Ion Channel *Anal. Chem.* 2007, 79, 2207-2213; Bayley, H. et al. Droplet interface bilayers. *Mol. Biosyst.* 4, 1191-1208 (2008).

In certain embodiments, the signature events can be provided in a synthetic nanopore. Synthetic nanopores include, but are not limited to, nanopores comprising silicon nitride or graphene.

Probe molecules provided herein comprise terminal extensions at one or both of their 5' and/or 3' termini. Without seeking to be limited by theory, it is believed that these terminal extensions provide useful functions that include, but are not limited to, trapping of the probe/target complex into the nanopore at a high rate (i.e. the number of signature events per unit target concentration per unit recording time). The trapping rate directly determines the sensitivity. In the same target concentration and the same recording time, a higher trapping rate gives a more precise sensing result. Without seeking to be limited by theory, it is also believed that these terminal extensions provide useful functions that include, but are not limited to, inducing the voltage-driven dissociation of the probe/target complex. This dissociation function generates a signature event that can be used to discriminate interactions of the probe with the target from other components in the mixture, thereby ensuring the selectivity or specificity.

Probe terminal extensions can comprise a charged polymer of any length. In certain embodiments, the polymer can be a negatively charged single-stranded nucleic acid. Advantages of such nucleic acid terminal extensions include, but are not limited to, extremely low cost of synthesis and controllable charge by pH, salt concentration and temperature. Such nucleic acid extensions can comprise homopolymers, heteropolymers, copolymers or combinations thereof. In certain embodiments, the lengths of such nucleic acid terminal extensions can range from about 1 or 2 nucleotides to about 50 nucleotides. In still other embodiments, the nucleic acid extensions can range in length from about 5 to about 40 nucleotides, about 15 to about 35 nucleotides, or from about 20 to about 35 nucleotides. An exemplary terminal extension provided herewith is homopolymer poly(dC)$_{30}$. However, a heteropolymeric sequence, including but not limited to, di- or tri-nucleotide heteropolymers such as CTCTCTCT . . . , or CATCATCAT . . . , can also be used. In certain embodiments, co-polymers comprising abases or polyethylene glycol (PEG) can be used in the terminal extension. These co-polymers, or domains thereof in a terminal extension, can confer new functions on the terminal extension of the probe. An abase is a nucleotide without the base, but carries a negative charge provided by the phosphate. As the dimension of abase is narrower than normal nucleotides, it may generate a signature event signal different from that formed by the neighbor nucleotides. PEG is not charged. Without seeking to be limited by theory, it is believed that when the PEG domain in a nucleic acid sequence is trapped in the pore, it can reduce the driving force, thus precisely regulating the dissociation of the probe/target complex.

Probe terminal extensions can also comprise a polypeptide. The richer choice of amino acids makes the sequence and functionality of the polypeptide terminal extension more programmable than an oligonucleotide terminal extension. For example, polypeptide terminal extensions allow insertion of charged amino acids in the optimized positions to generate more distinguishable probe/target signature events. While not seeking to be limited by theory, it is believed that the probe/target complex can be selectively trapped using a probe comprising a positively charged polypeptide terminal extension under an appropriate voltage while all other negatively charged non-target oligonucleotides in the mixture are prevented from entering into the pore, resulting in ultra-selective detection. In certain embodiments, the polypeptide terminal extensions can comprise two, three, four, or more amino acid residues that can carry a positive charge (i.e. lysine and/or arginine and/or histidine). In certain embodiments, sufficient numbers of positively charged residues are included in the polypeptide terminal extension to provide a net positive charge when said probe is hybridized to a target oligonucleotide. In certain embodiments where probes comprising terminal extensions with positive charges conferred by residues such as lysine, arginine or histidine, performance of the associated nanopore based detection methods can be enhanced under acidic conditions (i.e. when the pH value is less than 7) or conditions where the residue will be protonated. Thus, the use of such probes at pH values of about 1 to about 6.9, 1 to about 6.0, about 1 to about 5.5, about 3 to about 5.5, and the like. In certain embodiments, the lengths of such polypeptide terminal extensions can range from about 1 or 2 residues to about 30 residues. In still other embodiments, the polypeptide extensions can range in length from about 5 to about 20 residues, about 8 to about 20 residues, or from about 8 to about 15 residues. In an exemplary embodiment, an HIV-TAT polypeptide comprising positively charged arginine and lysine residues can be used as the terminal extension. In certain embodiments, the center domain of the probe that is complementary to the target oligonucleotide can comprise a peptide nucleic acid that is covalently linked to a terminal extension comprising amino acids that carry a positive charge. In certain embodiments, a center domain comprising a peptide nucleic acid is used in conjunction with a terminal extension comprising amino acids that carry a positive charge to provide a net positive charge when said probe is hybridized to a target oligonucleotide. In certain embodiments, polypeptide terminal extensions comprising amino acids with aromatic side chains including, but not limited to, phenylalanine, tryptophan, tyrosine, thyroxine, and the like, can be incorporated into the polypeptide terminal extensions. While not seeking to be limited by theory, it is believed that such aromatic amino acids can interact with the pore through aromatic stacking and provide for useful changes in the signature obtained in nanopore based detection methods.

Without seeking to be limited by theory, it is believed that if there are a sufficient number of positively-charged amino acids in the polypeptide terminal extension such that the net charges of the target oligonucleotide/probe complex are still positive when the probe comprising the terminal extension is hybridized to the target oligonucleotide, then the entire target oligonucleotide/probe complex will form a strong dipole molecule. It is believed that the positively-charged peptide domain of the probe dipole will be both pushed by the positive voltage (cis grounded) and attracted by the negative ring at the trans opening, guiding the trapping of the oligonucleotide/ probe complex into the pore. At the positive voltage, any other free nucleic acids components will be repulsed from entering the pore due to the negative charge that is carried by the free, unhybridized nucleic acids. This significantly reduces signals by free nucleic acid components, such that the majority of the observed current blockage events are either due to the trapping of the oligonucleotide/probe complex or to the translocation of the probe.

In certain embodiments, the oligonucleotide/probe complexes with a net positive charge can be directed to a nanopore with a negatively-charged ring at the trans-opening of the pore. In this context, a trans opening of a pore is understood to be that portion of the pore from which a molecule would emerge whereas a cis opening of a pore from which a molecule would enter. In these embodiments, it is understood that a negative charged ring at the trans-opening of the pore can be obtained by using any type of nanopore that has been suitably synthesize and/or derivatized so as to have a negative charged ring at the trans-opening of the pore. Such nanopores with a negatively charged ring at the trans opening of the pore include, but are not limited to, protein nanopores and synthetic nanopores. Protein nanopores with a negatively charged ring at the trans opening of the pore include, but are not limited to, engineered variants of an alpha-hemolysin protein. In certain embodiments, the engineered alpha hemolysin variant can comprise a *Staphylococcus aureus* alpha hemolysin containing a K131D, a K131E, or a K131H amino acid substitution. Exemplary and non-limiting *Staphylococcus aureus* alpha hemolysin wild type sequences are provided herein (SEQ ID NO:20, nucleic acid coding region; SEQ ID NO:21: protein coding region) and available elsewhere (National Center for Bioinformatics or GenBank Accession Numbers M90536 and AAA26598). An exemplary and non-limiting *Staphylococcus aureus* alpha hemolysin variant comprising a K131D substitution is provided as SEQ ID NO:22. In certain embodiments, the engineered alpha hemolysin variant can comprise a suitably derivatized variant that is derivatized with moieties that provide for a negatively charged ring at the trans opening of the pore. An exemplary wild type *S. aureus* alpha hemolysin protein that can be substituted or derivatized to provide for a protein nanopore with a negative charged ring at the trans-opening of the pore is provided herewith as SEQ ID NO: 21. However, variants of other hemolysins capable of forming pores can be substituted or derivatized to provide for a protein nanopore with a negative charged ring at the trans-opening of the pore. Synthetic nanopores with a negatively charged ring at the trans opening of the pore are also provided. In certain embodiments, such synthetic nanopores with a negatively charged ring at the trans opening of the pore include, but are not limited to, silicon nitride or graphene nanopores that have been suitably derivatized with moieties that provide for a negatively charged ring at the trans opening of the pore.

The center domain of probes provided herein is used to capture the target molecule. In certain embodiments, the center domain can be fully complementary or partially complementary to the target sequence. In certain embodiments, a center domain can comprise an oligonucleotide comprising natural nucleotides (A, T, G, C (DNA) or a, u, g, c (RNA)), and/or artificial nucleotides including, but not limited to, nucleosides such as inosine, xanthosine, 7-methylguanosine, Dihydrouridine, and 5-methylcytidine. In certain embodiments, the center domain can comprise a locked nucleic acid (LNA) or a peptide nucleic acid (PNA). Locked nucleic acids comprise RNA derivatives where the ribose ring contains a methylene linkage between the 2'-oxygen and the 4'-carbon. Peptide nucleic acids (PNA) comprise a peptide backbone with nucleobase side chains. In certain embodiments, a LNA or a PNA center domain can comprise natural nucleobases (adenine, guanine, thymine, cytosine or uracil) and/or artificial nucleobases including, but not limited to, hypoxanthine, xanthosine, 7-methylguanine, 5,6-dihydrouracil, and 5-methyl cytosine. In certain embodiments, probe center domains comprising co-polymers of oligonucleotides, LNA, or PNA are provided. In certain embodiments, a center domain of a probe will have at least about 4, 6, 8, 10, 12, 14, 15, 16, 17, 18, 19, 20, 21, 22, 23, 24, or 25 nucleotide or nucleobase residues that are complementary to the target nucleic acid. In certain embodiments, a central region of a probe will have at least about 4, 6, 8, 10, 12, 14, 15, 16, 17, 18, 19, 20, 21, 22, 23, 24, or 25 to any of about 30, 35, 40, or 50 nucleotide or nucleobase residues that are complementary to the target nucleic acid. In certain embodiments, synthetic nucleotides or nucleobases inserted in the sequence can precisely adjust the hybridization energy with the target, such that one can distinguish the characters of targets such as single-nucleotide polymorphism, methylation, or interaction between miRNA and its target messenger RNA.

A variety or target nucleic acids or oligonucleotides that can be detected and distinguished from non-target nucleic acids by the probes, nanopores, kits comprising the probes and nanopores, and associated methods of use probes, provided herein. In certain embodiments, the target can be a nucleic acid or a fragment thereof from cells, body fluid, tissues, bacteria, or a virus. In certain embodiments, the target can be a PCR products or a synthetic oligonucleotide. In certain embodiments, a target can comprise a genomic DNA, an mRNA, a pre-mature or mature miRNA, an artificial miRNA, non-coding DNA or RNA, a nucleic acid biomarker, or a synthetic aptamer. In certain embodiments, a miRNA targets may come from the RNA extraction from bio-fluid from any tissues such as plasma and formalin-fixed and paraffin-embedded tissues. In certain embodiments, a target nucleic acid can comprise be a nucleic acid fragment complexed with any of a nucleic acid binding protein, an antibody, or an aptamer bound with a target protein. In certain embodiments, a target nucleic acid can comprise be a nucleic acid fragment complexed with a low molecule weight compound, including, but not limited to, a drug. In certain embodiments, targets can include sequences with mutations, with single-nucleotide polymorphisms, or with chemical modifications such as methylation and phosphorylation.

EXAMPLES

Example 1

Detection of miR-155, a Lung Cancer Biomarker

The invention further provides an exemplary nanopore sensing system for detection of miR-155, a lung cancer biomarker. The nanopore sensing system includes an α-hemolysin transmembrane protein pore and a pre-designed probe for miR-155. The probe is a DNA multiple-block copolymer with its central domain complementary to the target miR-155, and at least one poly(dC)$_{30}$ extension at 3'-, 5'-, or both terminals functioning as signal tags. Table 1 lists the sequences of miR-155 and the exemplary probes with the tri-block copolymer, $P_{155}$ as preferred.

TABLE 1

Sequences of miRNAs and their probes

| miRNA | Probe | Sequence |
|---|---|---|
| mir-155 | | 5'-UUAAUGCUAAUCGUGAUAGGGG-3' (SEQ ID NO: 1) |
| | $P_{nt}$ | 5'-CCCCTATCACGATTAGCATTAA-3' (SEQ ID NO: 2) |
| | $P_{5'-C30}$ | 5'-C$_{30}$-CCCCTATCACGATTAGCATTAA-3' (SEQ ID NO: 3) |
| | $P_{3'-C30}$ | 5'-CCCCTATCACGATTAGCATTAA-C$_{30}$-3' (SEQ ID NO: 4) |
| | $P_{155}$ | 5'-C$_{30}$-CCCCTATCACGATTAGCATTAA-C$_{30}$-3' (SEQ ID NO: 5) |

Figure 4:
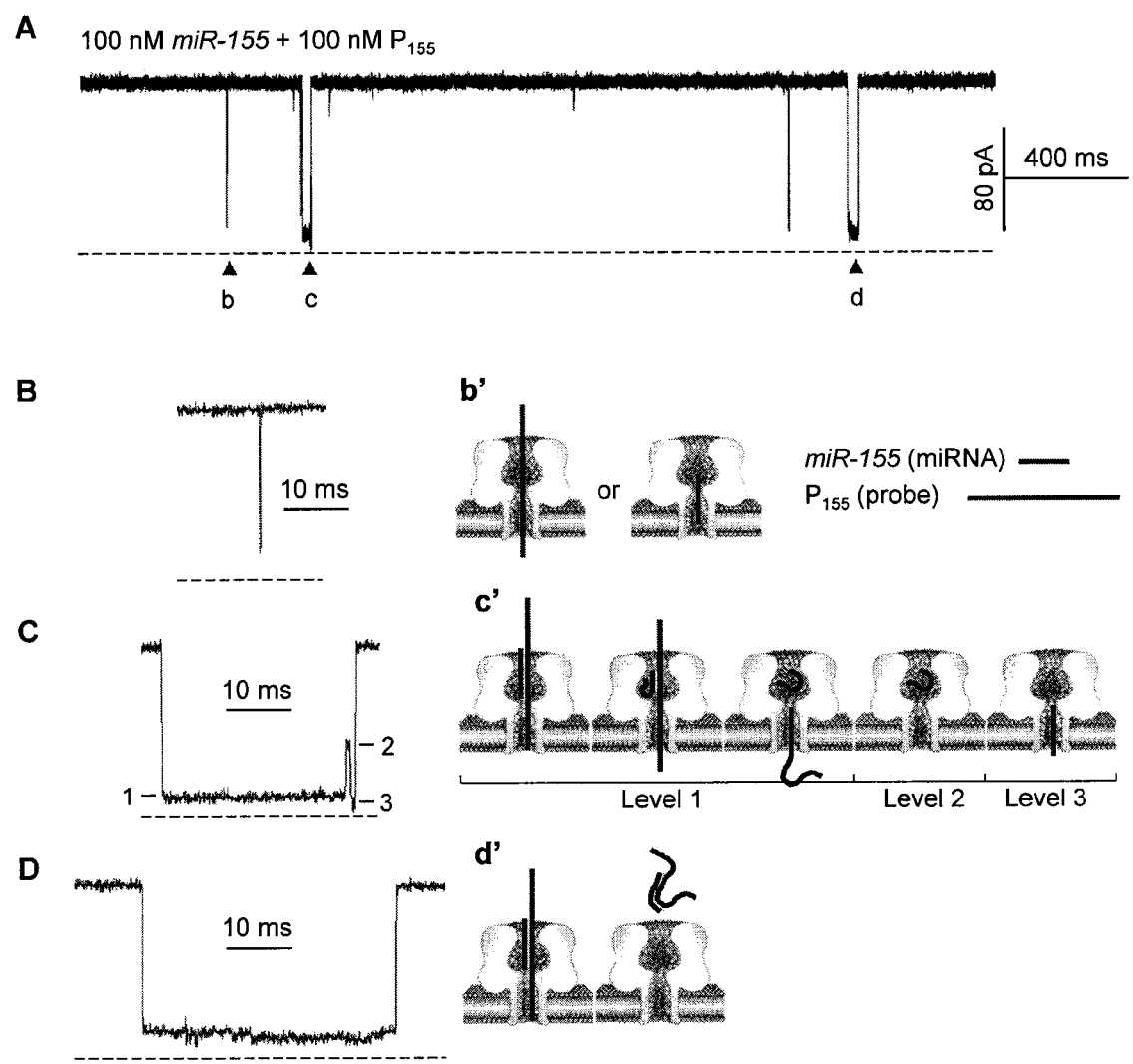
FIGS. 4(A) to (D) illustrate an exemplary detection of miR-155 with the inventive probe, $P_{155}$.

During an exemplary sensing process, a mixture of miR-155/$P_{155}$ is added to the cis side of the pore, a current trace with a series of short- and long-lived current blocks can be recorded, as shown in FIG. 4a, while being monitored in 1 M KCl at +100 mV. The spike-like short blocks, labeled as b in FIG. 4a and also shown in FIG. 4b, have duration of 220±21 μs and almost fully reduce the pore conductance with a relative conductance $g/g_0$=0.16, where g and $g_0$ are conductance of blocks and unoccupied nanopore. Both the duration and conductance are similar to that of blocks by miR-155 and $P_{155}$ alone, thus the short blocks in the mixture are associated with the rapid passage of single-stranded free miR-155 or $P_{155}$ through the pore, as illustrated in FIG. 4b'.

In contrast to short blocks, the long blocks, labeled as c and d in FIG. 4a, in the recording persist for 250±58 ms. One type of long blocks, labeled as c in FIG. 4a, features three sequential conductance levels, Level 1→Level 2→Level 3 (expended in FIG. 4c). This type of blocks is not observed when either miR-155 or $P_{155}$ alone is presented, indicating that it is originated from the miR-155/$P_{155}$ hybrid (miR-155·$P_{155}$). Level 1 almost fully reduces the conductance to $g/g_0$=0.15. This conductance level is consistent with a configuration that miR-155·$P_{155}$ is trapped in the pore from the wider opening (cis), with either 3'- or 5'-signal tag of $P_{155}$ occupying the narrowest β-barrel (FIG. 4c' level 1). The signal tag in the β-barrel can induce unzipping of miR-155·$P_{155}$, driven by voltage. The unzipping time, or the duration of Level 1, is comparable to previously reported time scales for DNA unzipping in the pore, e.g. ~435 ms for unzipping a 50 bps dsDNA at +140 mV, and ~40 ms for a 10 bps hairpin DNA at +90 mV. The unzipping process was further evidenced by the discrete transition from Level 1 to Level 2. Level 2 lasts 410±20 μs and its conductance significantly increases to $g/g_0$=0.42 (FIG. 1c' level 2). This partial block can not be interpreted as an oligonucleotide occupying in the β-barrel. It is very likely that, after unzipping of miR-155·$P_{155}$ followed by translocation of $P_{155}$, mir-155 can be temporarily confined in the nanocavity of the pore. It has been verified that a single-stranded oligonucleotide residing in the nanocavity can generate such a partial block[33,34]. The miR-155 molecule in the nanocavity finally traversed the β-barrel, generating Level 3 which fully reduces the conductance to $g/g_0$=0.08 (FIG. 4c). The duration of Level 3 is 270±30 μs, close to the 220 μs for short blocks by mir-155 alone, and consistent with the time scale of ~400 μs for translocation of a 75 bases RNA at +120 mV,[35] and 800 μs for a 210 bases RNA at +120 mV.[36] The duration of Level 3 becomes shortened as the voltage increases, further supporting the translocation of a single-stranded oligonucleotide for this conductance level.

In addition to the multi-conductance long blocks, the long blocks with single conductance level at $g/g_0$=0.15 (labeled as d in FIG. 4a and expended in FIG. 4d) have also been observed. This type of long blocks may occur when the arrested miR-155·$P_{155}$ exits the pore from the cis entry without unzipping.

The invention teaches that the characteristic long blocks can serve as signature events for identifying single molecules of target miRNAs. From the frequency of signature events ($f_{sig}$), the target miRNA can be quantified using Eq. 1 (Methods in Supplementary Materials, provided below in Example 2), $$f_{sig} = k_{on} \frac{([miR]_0 + [P]_0 + K_d) - \sqrt{([miR]_0 + [P]_0 + K_d)^2 - 4[miR]_0[P]_0}}{2} \quad (1)$$

Figure 5:
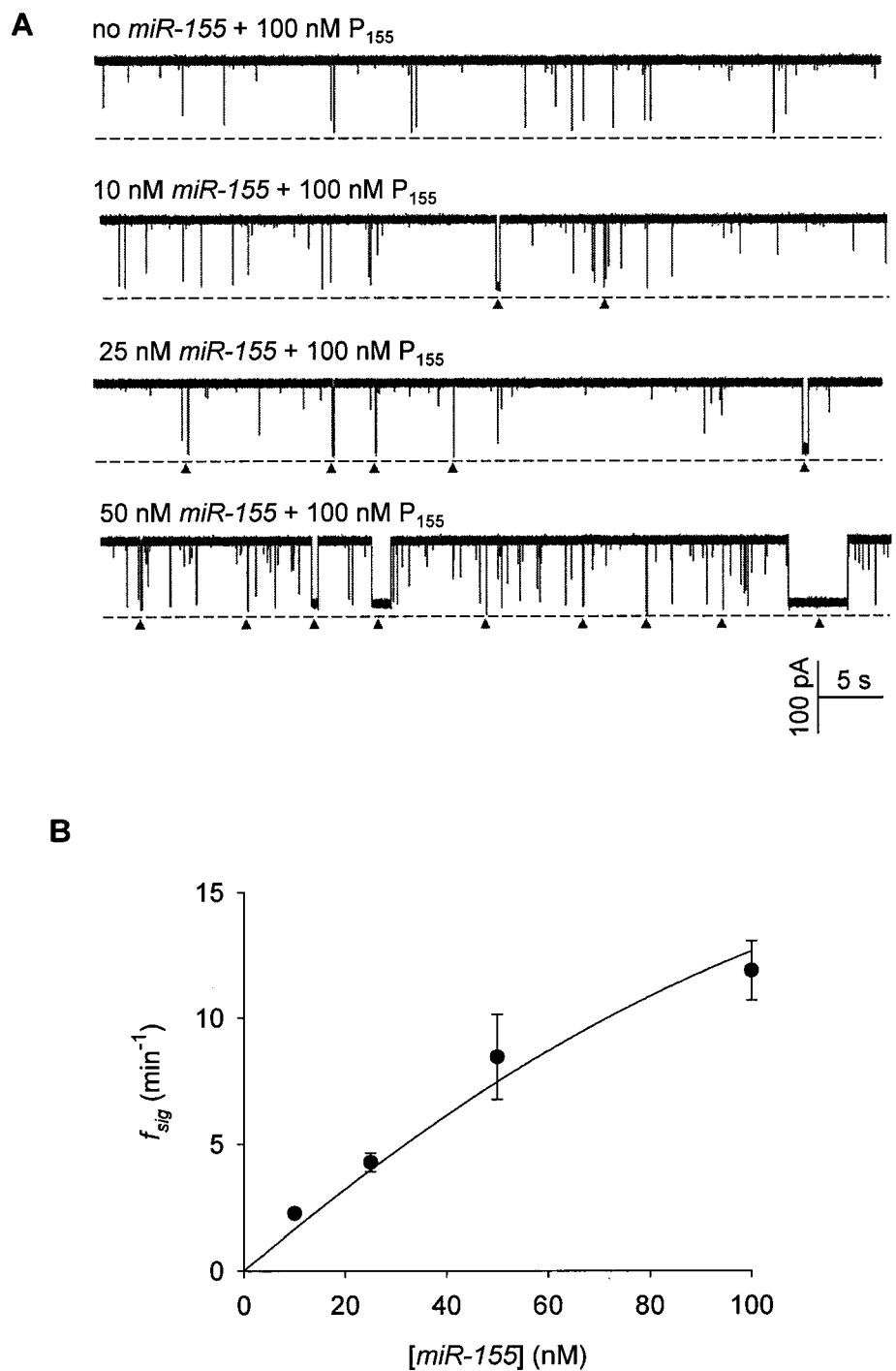
FIGS. 5(a) and (b) illustrate the invention employed in the quantification of miRNAs using the nanopore sensor. a. Current traces in the presence of 100 nM $P_{155}$ and different concentrations of miR-155. The signature events for miR-155·$P_{155}$ hybrid interacting with the pore are marked with red arrows. b. Correlation between the miR-155 concentration [miR-155] and the frequency of signature events ($f_{sig}$). Significance (p<0.01) is valid between detections in any two miR-155 concentrations. The $f_{sig}$-[miR-155] curve is fitted using Eq. 1.

In Eq. 1, $[miR]_0$ and $[P]_0$ are the initial concentrations of miRNA and the probe, $k_{on}$ is the occurrence rate of signature events and $K_d$ is the dissociation constant for miR·P in the solution. When $[miR]_0 \ll [P]_0$, $f_{sig} \approx k_{on}[miR]_0$. The current traces indeed show more frequent miR-155·$P_{155}$ signature events as the miR-155 concentration increases (FIG. 5a). The $f_{sig}$-[miR-155] data can be best fitted using Eq. 1, with $K_d$=30 nM and $k_{on}$=3.6×10$^6$ M$^{-1}$s$^{-1}$ (FIG. 5b). According to the literature[8], the mean concentrations of circulating miRNAs were 158.6 ng/mL (~25 nM) for the lung cancer group versus 68.1 ng/mL (~10 nM) for the control group. Therefore we compared the $f_{sig}$ values at 10 nM and 25 nM mir-155 (FIG. 5b). Analysis indicates that the two levels of miRNA concentration can be separated (p<0.005), suggesting that the inventive method has the potential to differentially detect miRNA levels in lung cancer patients.

The invention also provides an exemplary process employing the inventive nanopore sensing system to differentiate highly similar miRNA sequences, let-7a and let-7b. let-7a and let-7b are members of the Let-7 tumor suppressing miRNA family[4-6]; and the two Let-7 members only contain different nucleotides at the position 17 and 19, which are adenines in let-7a and guanines in let-7b. The inventive probes $P_a$ and $P_b$ are designed for let-7a and let-7b respectively with sequences listed in Table 2.

TABLE 2

Sequences of let-7a and let-7b and their probes

| miRNA | Probe | Sequence |
|---|---|---|
| Let-7a | | 5'-UGAGGUAGUAGGUUGUAUAGUU-3' (SEQ ID NO: 6) |
| | $P_a$ | 5'-C$_{30}$-AACTATACAACCTACTACCTCA-C$_{30}$-3' (SEQ ID NO: 7) |
| Let-7b | | 5'-UGAGGUAGUAGGUUGUGUGGUU-3' (SEQ ID NO: 8) |
| | $P_b$ | 5'-C$_{30}$-AACCACACAACCTACTACCTCA-C$_{30}$-3' (SEQ ID NO: 9) |

Figure 6:
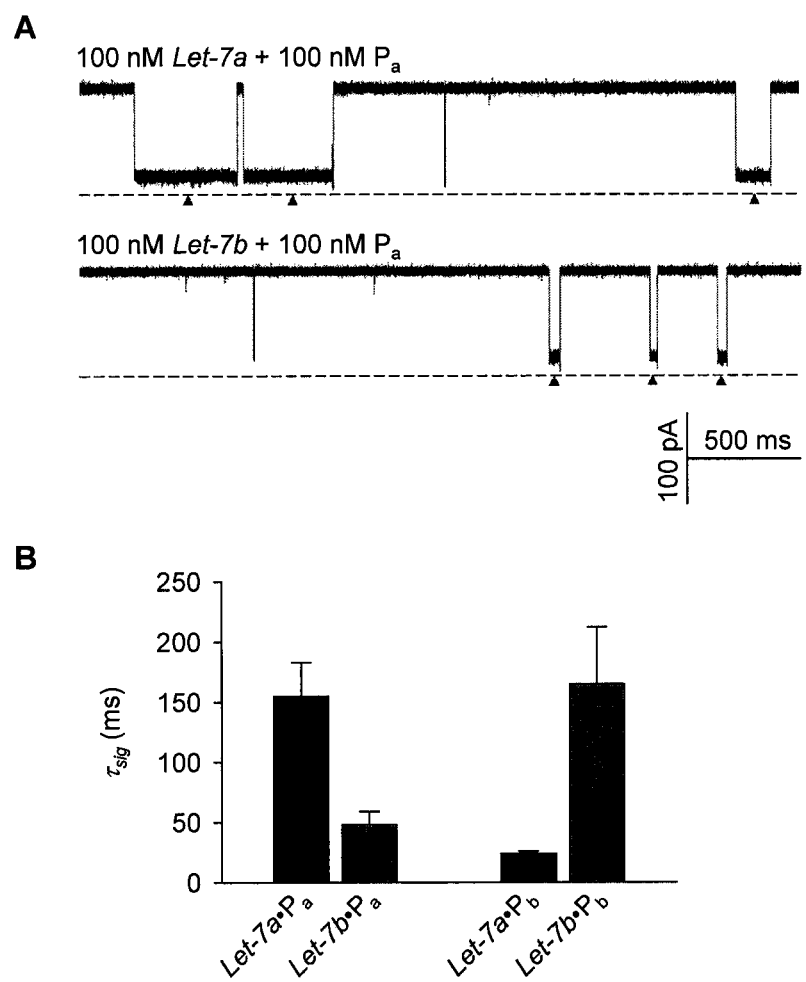
FIGS. 6(a) and (b) illustrate the invention employed in the differentiation of miRNAs with similar sequences. a. Current traces for detections of let-7a and let-7b using the probe $P_a$ (+120 mV). b. Durations of signature events ($\tau_{sig}$) for let-7a·$P_a$, let-7b·$P_a$, let-7a·$P_b$ and let-7b·$P_b$.

As shown in FIG. 6a and FIG. 6b, when using $P_a$ to detect each miRNA, the duration of signature events ($\tau_{sig}$) for let-7a·$P_a$ (without mismatch) is 155±28 ms, whereas $\tau_{sig}$ for let-7b·$P_a$ (with 2-nt mismatches) is significantly shortened to 48±11 ms (p<0.005). Similarly, when using $P_b$ to detect both miRNAs, $\tau_{sig}$ for let-7b·$P_b$ (without mismatch) is 165±47 ms, significantly longer than the 24±2 ms for let-7a·$P_b$ (with 2-nt mismatches) (p<0.005) as shown in FIG. 6b. The significant differences in durations can be interpreted that the mismatches significantly weaken the hybridization interaction between miRNA and the probe. When placed in the identical electrical field, the hybrid containing mismatches needs lower energy than fully matched hybrid to unzip. Thus, the inventive nanopore sensing system is able to differentiate single mismatches based on the unzipping time, thus demonstrating the potential to detect miRNAs with similar sequences and SNPs.

Figure 7:
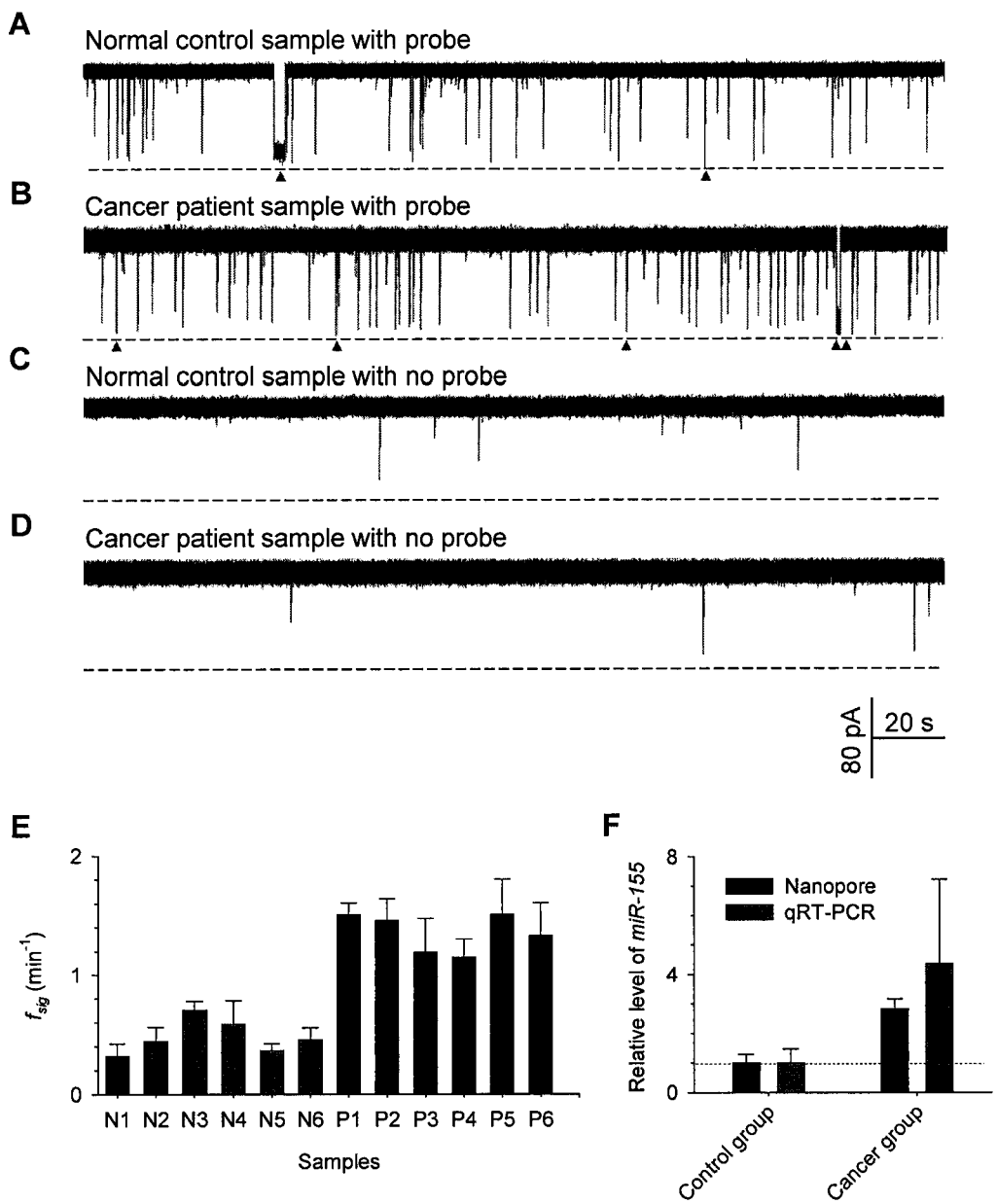
FIGS. 7(a) to (f) illustrate the invention employed in the detection of miR-155 in lung cancer patients' plasma. a through d, the signature events were found in current traces for total plasma RNAs from normal volunteers (a) and lung cancer patients (b) in the presence of 100 nM $P_{155}$ probe, but not observed in the absence of $P_{155}$ (c and d). The traces were recorded in 1 M KCl at +100 mV. e. Frequencies of miR-155 signature events ($f_{sig}$) from six normal individuals (N1 to N6) and six patients with lung cancer (P1 to P6). Each sample was measured n times (n≥4) with independent nanopores. The data was given as mean±SD. The patient conditions are, P1, metastatic squamous lung carcinoma; P2, recurrent small-cell cancer; P3, early stage of small-cell carcinoma, status post chemotherapy and radiation; P4, early stage of small-cell cancer, status post chemotherapy; P5, late stage non-small cell carcinoma, statue post resection and chemotherapy; P6, late stage adenocarcinoma, status post chemotherapy. f. Relative miR-155 levels in normal group (left) and lung cancer patient group (right), measured with the nanopore sensor and qRT-PCR. The means with SD were shown.

The invention further provides an exemplary process of detecting plasma miR-155 in lung cancer patients with the inventive nanopore sensing system. During the exemplary process, the peripheral blood samples were obtained from six lung cancer patients and six normal volunteers with a local IRB approval. Total plasma RNAs containing miRNAs were extracted from 350 µl of each plasma sample using miRVana PARIS Kit (Ambion), with a final elution volume of 100 µl, which were than divided into two aliquots (50 µl) for the nanopore and RT-PCR assay[44]. One aliquot was pre-mixed with $P_{155}$ and directly added to the 2-ml recording solution in the nanopore chamber. The nanopore current retain a low level of noise even in the presence of plasma samples, and distinct short and long blocks (marked with red arrows) can be indentified in both the control group (FIG. 7a) and lung cancer group (FIG. 7b). The characteristic long blocks, including both with multiple conductance and single conductance, features the same conductance profiles and similar properties to that for synthetic miR-155 RNA in FIG. 1a. In the absence of $P_{155}$, no such types of long blocks can be observed (FIGS. 7c and d), but short blocks were found for translocation of single-stranded oligonucleotides such as free miRNAs (FIGS. 7c and d). Overall, the characteristic long blocks could be attributed to miR-155·$P_{155}$ hybrids and serve as signature events for single miRNA molecules detection.

The frequency of miR-155 signature events $f_{sig}$ for all samples in the lung cancer patient group varies between 1.15-1.51 $min^{-1}$, with a mean of 1.40±0.16 $min^{-1}$ (FIG. 7e). This level was significantly higher than $f_{sig}$ in the control group that ranges between 0.32-0.70 $min^{-1}$ with a mean of 0.48±0.14 $min^{-1}$ (FIG. 7e). Since all samples were prepared following a standard procedure (Methods in Supplementary Materials), it should be valid to compare relative miRNA levels in two groups. When the mean $f_{sig}$ value in normal plasma was set as 1, the folds of miR-155 in lung cancer plasma were compared with the two methods. FIG. 7f showed that the relative mir-155 level in lung cancer patients was 2.79 with the nanopore sensor (p<0.001). By comparison, the relative miR-155 level was 4.72 with RT-PCR method (p<0.02) with greater variability. Therefore, both nanopore and RT-PCR assay indicated a significant elevation of miR-155 in lung cancer patient plasma although there is a 1.69 fold difference. As the nanopore method does not require labeling and amplification, this may be a reason for smaller variability in the nanopore assay (FIG. 7f). Overall the nanopore sensor with engineered probes demonstrates the ability to detect circulating miRNAs in clinical lung cancer patients, which is verified by the independent RT-PCR method.

Example 2

Supplementary Information

Materials. Oligonucleotides including miRNAs and DNA probes were synthesized and electrophoresis-purified by Integrated DNA Technologies (Coralville, Iowa). Before testing, the mixtures of miRNA and DNA probe were heated to 90° C. for 5 minutes, then gradually cooled down to room temperature and stored at 4° C. The RNase-free water was used to prepare RNA solution.

Setup and method of nanopore detection. This section has been well-documented earlier (Shim, J. W., Tan, Q., & Gu, L. Q. Single-molecule detection of folding and unfolding of a single G-quadruplex aptamer in a nanopore nanocavity. Nucleic Acids Res. 37, 972-982 (2009)). Briefly, the recording apparatus was composed of two chambers (cis and trans) that were partitioned with a Teflon film. The planar lipid bilayer of 1,2-diphytanoyl-sn-glycerophosphatidylcholine (Avanti Polar Lipids) was formed spanning a 100-150 nm hole in the center of the partition. Both cis and trans chambers were filled with symmetrical 1 M salt solutions (KCl) buffered with 10 mM Tris and titrated to pH 8.0. All solutions are filtered before use. Single α-hemolysin proteins were inserted into the bilayer from the cis side to form molecular pores in the membrane. All the oligonucleotides including miRNAs and DNA probes and clinical RNA samples were also added to the cis solution. To record the pore current, the cis solution was grounded and the voltage was given from the trans solution. In this convention, a positive voltage can drive the translocation of a negatively charged DNA through the pore from cis to trans. Single-channel currents were recorded with an Axopatch 200A amplifier (Molecular Device Inc. Sunnyvale, Calif.), filtered with a built-in 4-pole low-pass Bessel Filter at 5 kHz, and acquired with Clampex 9.0 software (Molecular Device Inc.) through a Digidata 1332 A/D converter (Molecular Device Inc.) at a sampling rate of 20 kHz. The data were analyzed using Clampfit 9.0 (Molecular Device Inc.), Excel (MicroSoft) and SigmaPlot (SPSS) software.

The translocation of free miRNA or probe through the pore generated very short current block (~$10^1$-$10^2$ µs). Some short blocks showed partially reduced pore conductance, which may be due to the filtering of the recording at 5 kHz, or formed by the trapped oligonucleotide returning back to the cis solution (Maglia, G., Restrepo, M. R., Mikhailova, E., & Bayley, H. Enhanced translocation of single DNA molecules through +/− hemolysin nanopores by manipulation of internal charge. Proc. Natl. Acad. Sci. U.S.A. 105, 19720-19725 (2008). In our experiments, all short blocks including these partial blocks were collected for histogram construction. Since the translocation events (~$10^1$-$10^2$ µs) are well distinguished from the signature events (~$10^1$-$10^3$ ms), we simply used 1 ms as the boundary for separation of short and long events. Data were given as the mean±SD, based on at least three separate experiments (n>3). In the t-test, p<0.05 was considered as a significant difference between two groups. The electrophysiology experiments were conducted at 22±2° C.

Total RNA Extraction From Plasma and miRNA Quantification by qRT-PCR.

Peripheral blood samples were obtained at the University of Missouri Ellis Fischel Cancer Center with an IRB approval. Whole blood with EDTA preservative was centrifuged at 1,600 g for 10 min at room temperature and the plasma was transferred to new tubes. Total RNAs containing miRNAs was extracted from 350 µl of plasma using miRVana PARIS Kit (Ambion, Austin, Tex., USA) according to the manufacturer's protocol. The final elution volume was 100 µl.

A SYBR green-based quantitative RT-PCR assay was employed for miRNA quantification. In brief, 10 µl of total RNA sample containing miRNAs was polyadenylated by poly(A) polymerase (Ambion) and reverse transcribed to cDNA using SuperScript III Reverse Transcriptase (Invitrogen) according to the manufacturer's instructions with a poly (T) adapter primer (5'-GCGAGCACAGAATTAATAC- GACTCACTATAGGTTTTTTTTTTTTTTVN-3'; SEQ ID NO: 10)). Real-time PCR was performed using iQ SYBR Green Supermix (Bio-Rad, Hercules, Calif., USA) with the miR-155 specific forward primer (5'-TTAATGCTAATCGT-GATAGGGGT-3'; SEQ ID NO:11) and the sequence complementary to the poly(T) adapter as the reverse primer (5'-GCGAGCACAGAATTAATACGAC-3'; SEQ ID NO:12) in iQ5 Real-time PCR system (Bio-Rad, USA). The PCR was carried out as follows: after initial denaturation at 95° C. for 3 min, 40 cycles of 95° C. for 15 s and 60° C. for 1 min were followed. The relative level of miR-155 was calculated using $2^{-delta\ Ct}$ method where the level of normal plasma was normalized as 1. Data was presented as mean±SD of three independent experiments, and the differences were considered statistically significant at p<0.05 by using the Student's t-test.

Normalization of the nanopore and qRT-PCR data using spiked-in *C. elegans* miRNA miR-39 as control. We introduced spiked-in synthetic miRNA as control, to convincingly validate the nanopore sensor's capability of miRNAs detection in human samples. The spiked-in RNA oligonucleotide in the detection matches the sequence of *C. elegans* miR-39, a miRNA that is absent in the human genomes. 3.5 µL, of 1 nM synthetic miR-39 solution was introduced to each 350 µL plasma sample after addition of the 2× Denaturing Solution (miRVana PARIS Kit) to the plasma, thus the miR-39 concentration in plasma was 10 pM. The Denaturing Solution prevents RNAs from undergoing degradation by inhibiting endogenous plasma RNAases. For each sample, both miR-155 and spiked-in miR-39 were measured using the nanopore sensor and SYBR green-based qRT-PCR. The nanopore data and normalization result were shown in Table 9. In the nanopore detection, the probes for miR-155 and miR-39 were $P_{155}$ and $P_{39}$. We first measured the signature event frequencies, $f_{155}$ and $f_{39}$, of the hybrids miR-155·$P_{155}$ and miR-39·$P_{39}$ respectively. The variability of $f_{39}$ reflected the difference in miR-39 concentrations among samples after RNA extraction. Therefore the ratio of the two frequencies, $f_{155}/f_{39}$, should principally eliminate this variability. Finally, we used the Mean $f_{155}/f_{39}$ of six normal samples ($A_{normal}$) as the standard, and calculated each sample's relative miR-155 level by normalizing $f_{155}/f_{39}$ to $A_{normal}$, i.e. $f_{55}/f_{39}/A_{normal}$.

Correlation between miRNA concentration and frequency of signature events. In the deduction, "miR" represents miRNA; "P", probe; $K_d$, equilibrium dissociation constant for miR·P; $k_{on}$, occurrence rate constant of miR·P signature events; and $f_{sig}$, frequency of signature events. In the mixture of miRNA and probe, the equilibrium can be established the reactors miR and P and the product miR·P, $$miR + P \underset{}{\overset{K_d}{\rightleftharpoons}} miR \cdot P \quad \text{(Scheme 1)}$$

$K_d$ is determined by $$K_d = \frac{([miR]_0 - [miR \cdot P])([P]_0 - [miR \cdot P])}{[miR \cdot P]} \quad (S1)$$

where $[miR]_0$ and $[P]_0$ are total concentrations of miRNA and the probe, and $[miR \cdot P]$ is the concentration of miR·P. Thus the relationship of $[miR \cdot]$ and $[miR]_0$ is $$[miR \cdot P] = \frac{([miR]_0 + [P]_0 + K_d) - \sqrt{([miR]_0 + [P]_0 + K_d)^2 - 4[miR]_0 + [P]_0}}{2} \quad (S2)$$

The kinetics for trapping and unzipping of miR·P in the nanopore is (Scheme 2)

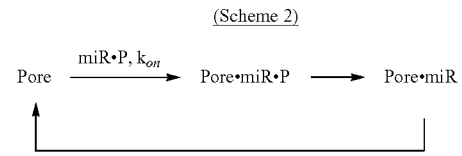

Because $f_{sig}$ is linearly related to $[miR \cdot P]$, $$f_{sig} = k_{on}[miR \cdot P] \quad (S3)$$

from Eq. S2 and Eq. S3, $$f_{sig} = k_{on} \frac{([miR]_0 + [P]_0 + K_d) + \sqrt{([miR]_0 + [P]_0 + K_d)^2 - 4[miR]_0[P]_0}}{2} \quad (S4)$$

Eq. S4 suggested that $f_{sig}$ is not in exact proportion to $[miR]_0$, the total concentration of the target miRNA. However, when $[miR]_0$ is considerably smaller than $[P]_0$, which is the case in our miRNA detection, Eq. S4 can be simplified as $$f_{sig} \approx k_{on}[miR \cdot P] \quad (S5)$$

In this condition, $f_{sig}$ is proportional to $[miR]_0$. Eq. S4 also suggested that $f_{sig}$ will ultimately become saturated. This is because $f_{sig}$ measures the capture frequency of miR·P, and the maximal concentration of miR·P ([miR·P]) can not be higher than that of the probe ($[P]_0$).

Figure 8:
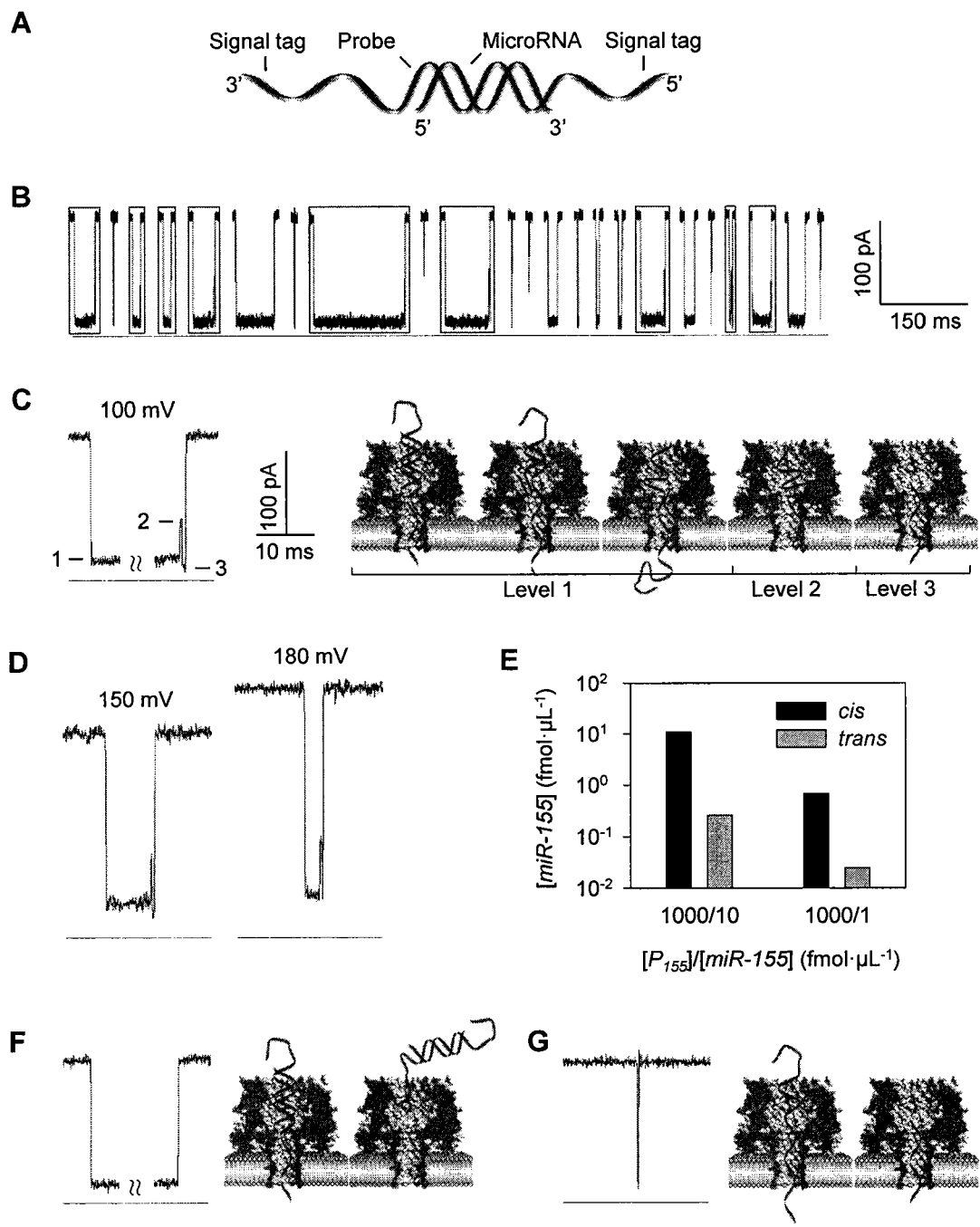
FIG. 8 A-G shows the capture of single miRNA molecules with a specific probe in the nanopore. A. Molecular diagram of the miRNA·probe hybrid; B. Sequentially-occurred nanopore current blocks in the presence of 100 nM miR-155/$P_{155}$ mixture in the cis solution. The recording solution contained 1 M KCl buffered with 10 mM Tris (pH 8.0). Traces were recorded at +100 mV. The identified current patterns and corresponding molecular mechanisms were depicted in panel c, f and g. The framed blocks demonstrated the multi-level current pattern depicted in panel c and d; c. Multi-level long block at +100 mV, generated by the miR-155·$P_{155}$ hybrid that was trapped in the pore, unzipped, followed by sequentially translocation of unzipped $P_{155}$ and miR-155 through the pore; d. Characteristic multi-level long blocks at +150 mV and +180 mV; e. qRT-PCR-detected miR-155 levels in cis and trans solutions after ~6 hours electrical recording at different concentrations of miR-155 and $P_{155}$ presented in the cis solution (Text in Supplementary Information); f. Single-level current pattern generated by a trapped mir-155·$P_{155}$ hybrid that exited the pore from the cis entrance without unzipping; g. Spike-like short block generated by translocation of un-hybridized miR-155 or $P_{155}$ from the cis solution.

Identification of miR-155 in trans solutions using RT-PCR. As shown in the model (FIG. 8), with the miRNA·probe complex unzipped in the pore, the separated probe and miRNA can sequentially translocate through the β-barrel to the trans solution. To verify this model, we employed RT-PCR to detect the unzipped miRNAs in the trans solution. However, the PCR method cannot discriminate if the trans miRNAs are from the unzipped miRNAs or from the free miRNA (un-hybridized) that simply translocated from the cis solution to the trans solution. We therefore added a much higher concentration of the probe than miRNA in the cis solution, so that most of the miRNAs molecules are bound with the probe and there is little free miRNA left, eliminating the translocation of free miRNA to the trans solution that can interfere with the PCR result. Our target was miR-155 and the probe was $P_{155}$. The target/probe concentrations were 0.1/1000, 1/1000 and 10/1000 (nM). After over 6 hours bilayer recording for many pores, 2 µL of both cis and trans solutions were subjected to polyadenylation, reverse transcription and RT-PCR to detect the concentration of miR-155 as indicated in the method described above. Meanwhile, a series of dilution of synthesized miR-155 were performed to construct standard curve for calibration. The cis and trans miR-155 were measured separately. In the case of 10/1000 (nM) miR-155/$P_{155}$ concentrations, the peaks of melting curves for trans RNA samples were the same as synthesized miR-155. According to the standard curve of miR-155, the miR-155 concentrations in trans solutions were 14, 34 and 63 aM ($10^{-8}$ M), indicating that a trace amount of miR-155 transported to the trans side of the pore.

Figure 9:
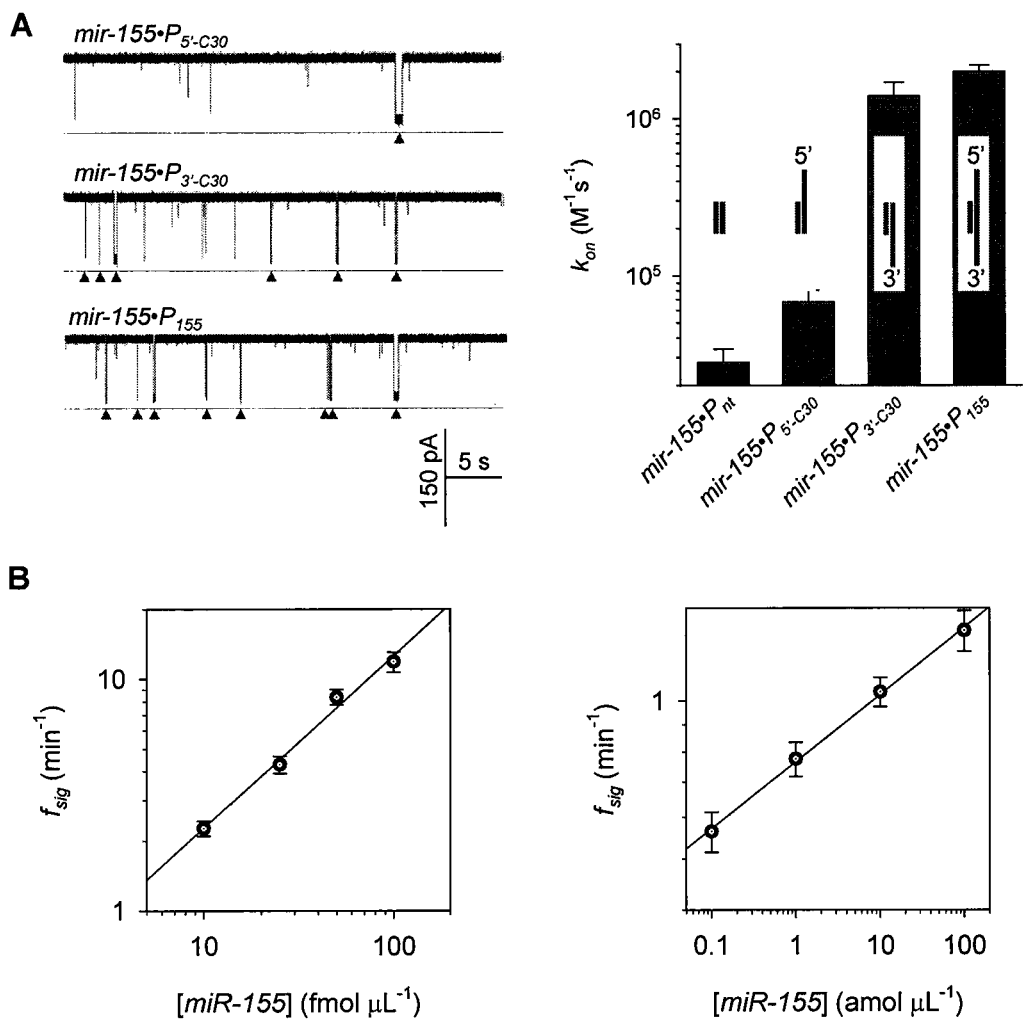
FIG. 9 A-B shows enhancing detection sensitivity by optimizing the probe sequence. A. Left, current traces showing the frequency of signature events for miR-155 hybridized with the probes $P_{5'-C30}$ (top), $P_{3'-C30}$ (middle) and $P_{155}$ (bottom), monitored at +100 mV in 1 M KCl. Right, the occurrence rate constant of signature events for miR-155 detection with different probes (Table 5). Significance (p<0.005) is valid between results with any two probes; B. Left, [miR-155]-$f_{155}$ correlation for target concentration ranging between 10-100 nM. Right, [miR-155]-$f_{155}$ correlation measured in 0.5 M/3 M (cis/trans) KCl asymmetrical solutions for much lower target concentration between 0.1-100 pM. Significance (p<0.01) was valid between detections at any two miR-155 concentrations.
Figure 10:
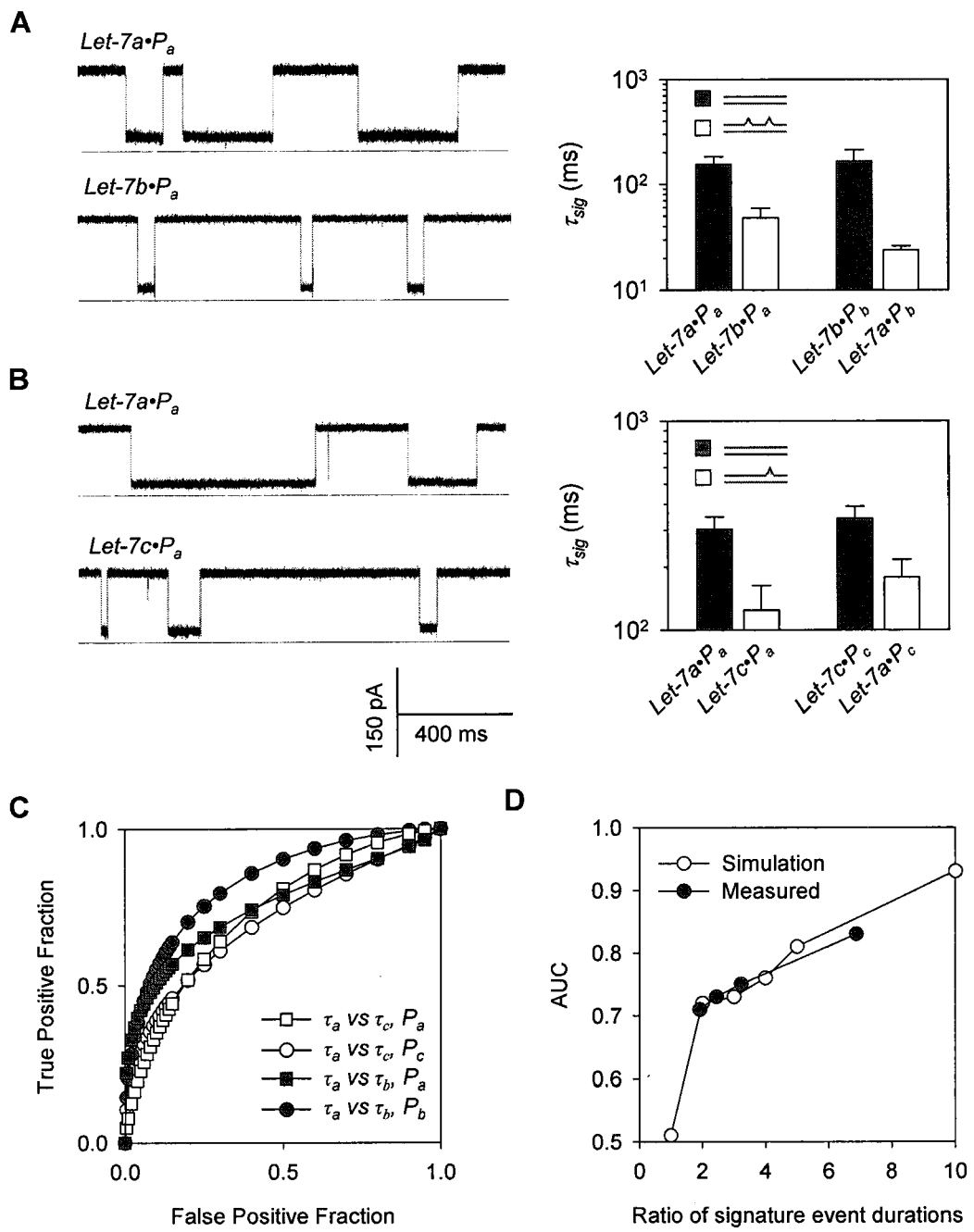
FIG. 10 A-D shows differentiation of let-7 miRNAs containing one or two different nucleotides. The sequence of let-7a, -7b, and -7c were given in Table 3). a. Detections of let-7a and let-7b using the probe $P_a$ or $P_b$ at +120 mV. Left, current traces, and right, comparison of signature event duration ($\tau_{sig}$); b. Detections of let-7a and -7c using the probe $P_a$ or $P_c$ at +100 mV. Left, current traces, and right, comparison of signature event duration ($\tau_{sig}$). Data was shown in Table 6; c. Receiver Operating Characteristic (ROC) curves for discrimination of events for miRNA·probe hybrids without (positive) and with mismatches (negative). □: let-7a·$P_a$/let-7b·$P_a$, ○: let-7b·$P_b$/let-7a·$P_b$, ■: let-7a·$P_a$/let-7c·$P_a$, and ●: let-7c·$P_c$/let-7a·$P_c$; d. Correlation between the areas under the ROC curves (AUC) and the duration ratio between fully-match events and mismatch events. ●: AUC measured from the ROC curves in panel c (Table 7), ○: AUC calculated from ROC analysis based on simulated datasets (FIG. 16 and Table 8). The events were generated with an exponentially distributed duration. The duration ratios of fully-match events (positive) and mismatch events (negative) were 1, 2, 3, 4, 5 and 10 respectively.
Figure 11:
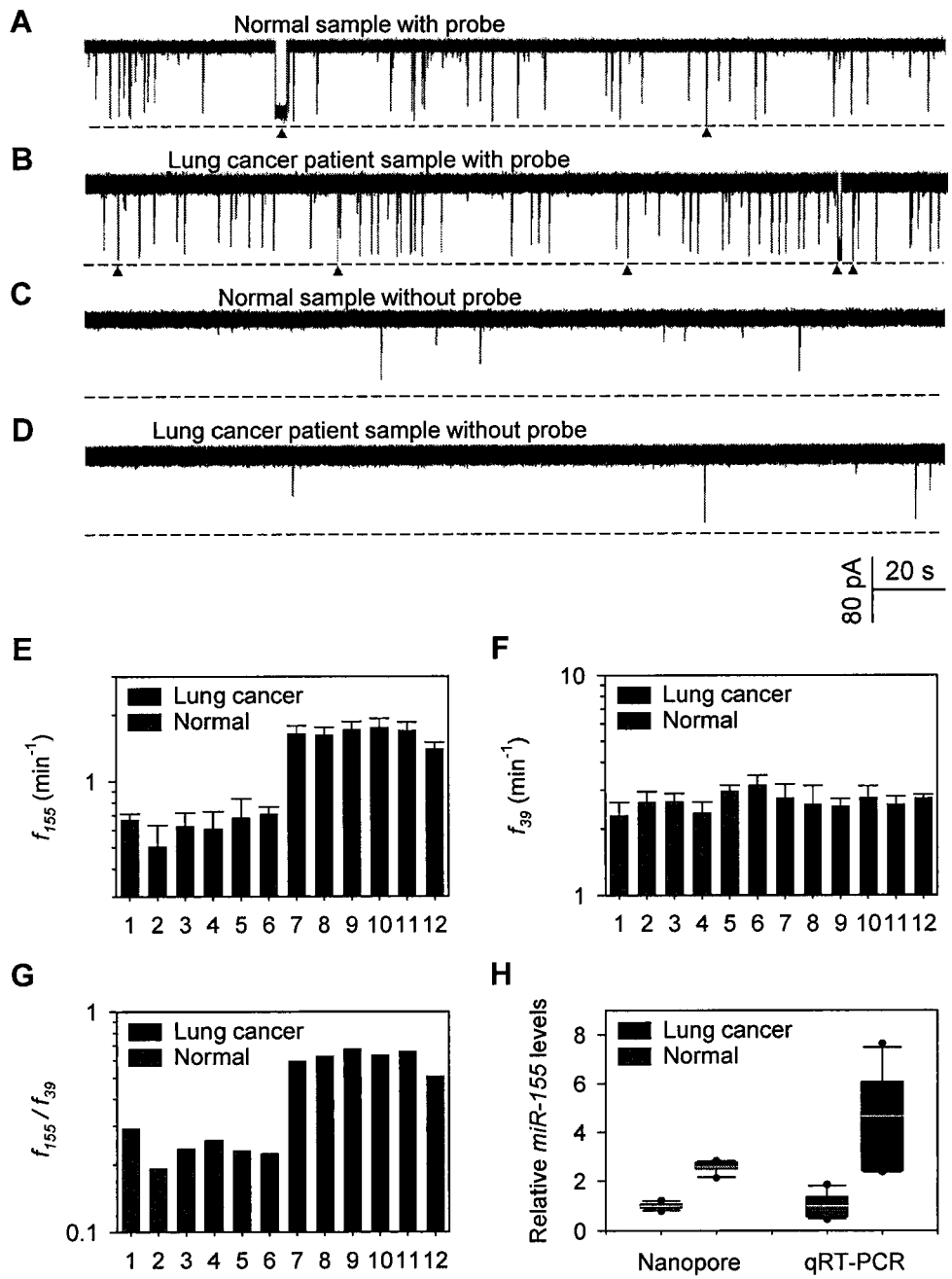
FIG. 11 A-H shows detection of miR-155 in lung cancer patients' plasma. a through d. Signature events found in current traces for total plasma RNAs from normal volunteers (a) and lung cancer patients (b) in the presence of 100 nM $P_{155}$ probe, no signature events observed in the absence of $P_{155}$ (c and d). The traces were recorded in 1 M KCl at +100 mV. e. Frequencies of miR-155 signature events ($f_{155}$) from six normal individuals (#1 to #6) and six patients with lung cancer (#7 to #12) in the presence of spiked-in synthetic miR-39. f. Frequencies of miR-39 signature events detected by $P_{39}$ (see the sequence in Table 3) from all sample used in e. Each sample was measured n times (n≥4) with independent nanopores. The data was given as mean±SD. The patient conditions were, #7, metastatic squamous lung carcinoma; #8, recurrent small-cell cancer; #9, early stage of small-cell carcinoma, status post chemotherapy and radiation; #10, early stage of small-cell cancer, status post chemotherapy; #11, late stage non-small cell carcinoma, statue post resection and chemotherapy; #12, late stage adenocarcinoma, status post chemotherapy. g. $f_{155}/f_{39}$ calculated from panel e and f. h. Box and Whiskers plot of relative miR-155 level in normal and lung cancer groups, measured with the nanopore sensor and qRT-PCR. The boxes mark the interval between $25^{th}$ and $75^{th}$ percentiles. The black lines inside the boxes denote the medians. The whiskers denote the interval between the $5^{th}$ and $95^{th}$ percentiles. Filled circles indicate data points outside the $5^{th}$ and $95^{th}$ percentiles. Data were given in Table 9.
Figure 12:
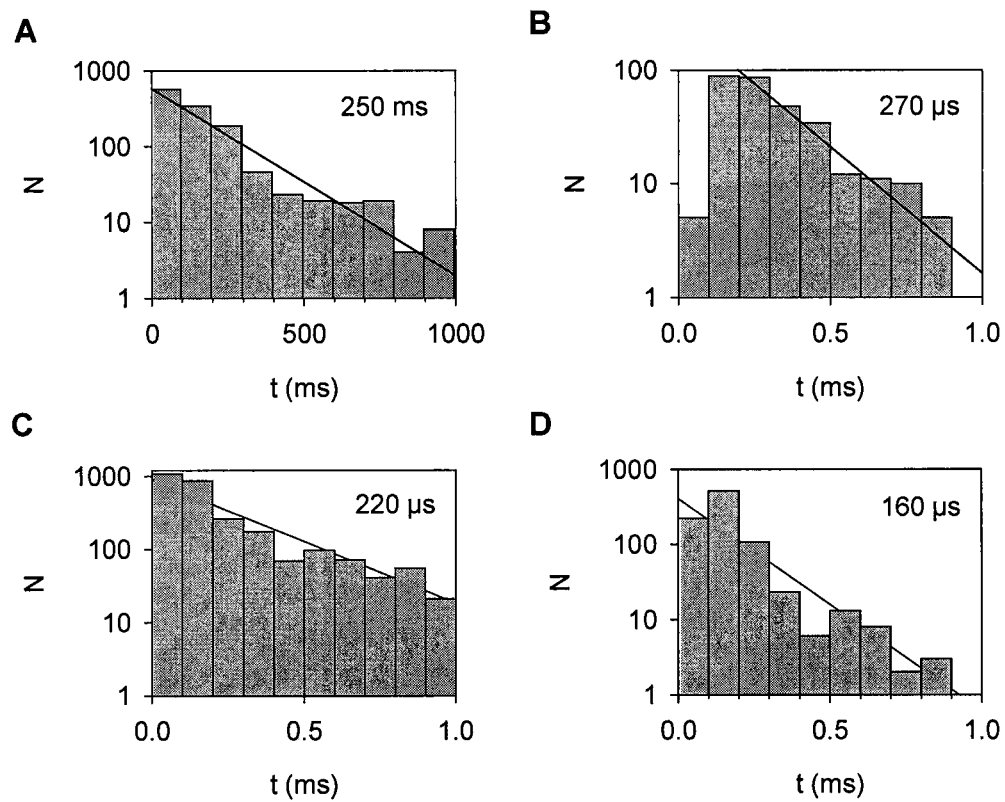
FIG. 12 A-D shows histograms of block durations. a. Signature blocks generated by the mir-155·$P_{155}$ hybrid. b. The short Level 3 state in the signature block. c. and d. Short blocks by translocation of miR-155 (c) and $P_{155}$ (d) alone. Data was obtained from current traces recorded in 1 M KCl at +100 mV.
Figure 13:
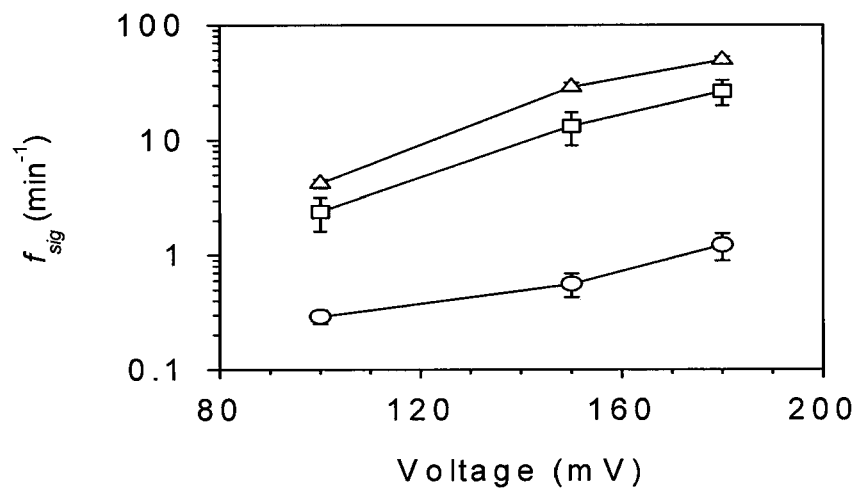
FIG. 13 shows voltage-dependent frequency of mir-155·$P_{155}$ signature events. Data was obtained from current traces recorded in 1 M KCl with 10 (Δ) and 25 (□) nM mir-155 in the presence of 100 nM $P_{155}$, and 10 pM mir-155 in the presence of 5 pM $P_{155}$ (○)
Figure 14:
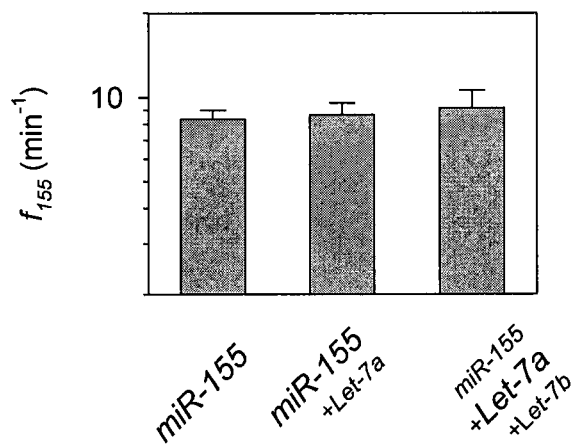
FIG. 14 shows the frequency of miR-155 signature events detected using $P_{155}$ (100 nM) in the presence of other synthetic miRNA components. The three bars represented miR-155 alone (50 nM), miR-155 in the presence of Let-7a (50 nM), and that in the presence of both Let-7a (50 nM) and -7b (50 nM). Data was obtained from current traces recorded in 1 M KCl at +100 mV.
Figure 15:
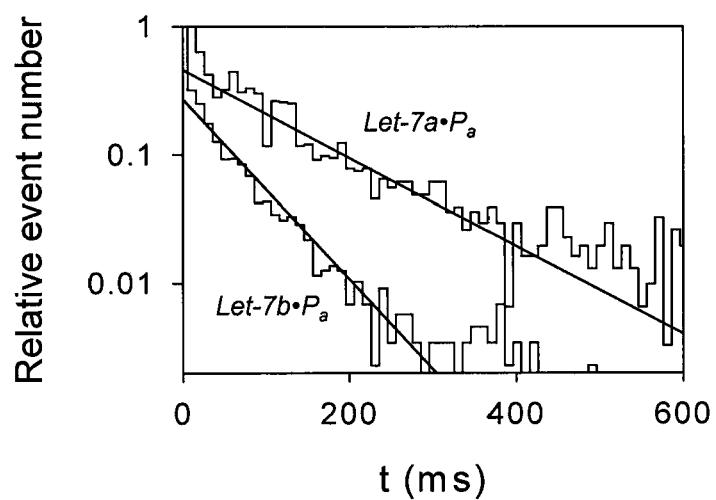
FIG. 15 shows duration histograms of signature events formed by Let-7a·$P_a$ and Let-7b·$P_a$ hybrids. Data was obtained from current traces recorded in 1 M KCl at +120 mV. a. Let-7a·$P_a$. b. Let-7b·$P_a$. Concentrations of all RNA and DNA components were 100 nM.
Figure 16:
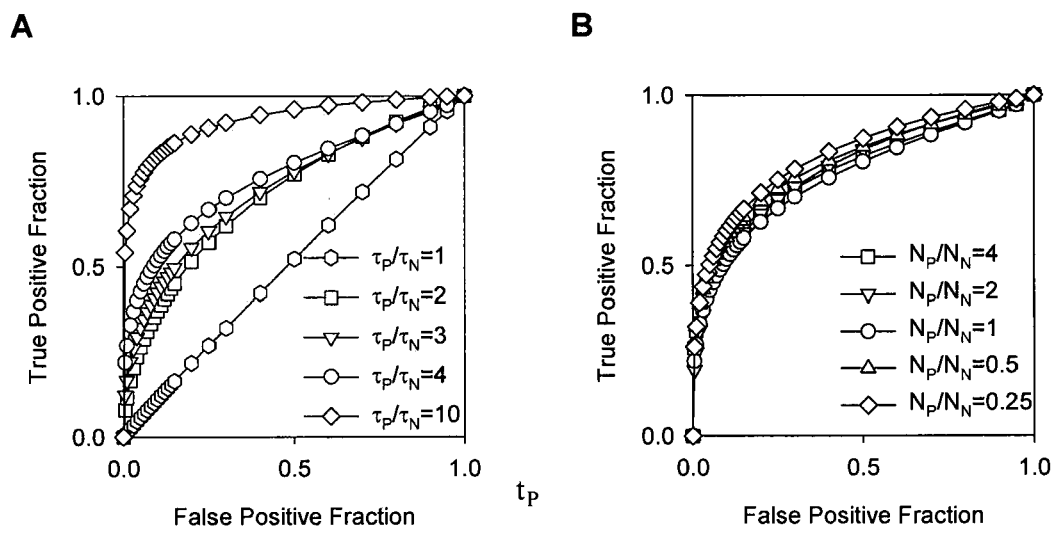
FIG. 16 A-B shows simulation on separation of fully-match (positive) and mismatch (negative) events based on event duration. a. ROC curves at various duration ratios. There were 400 events of both types participating in the analysis; b. ROC curves at various event number ratios of the two type of events. The duration ratio $\tau_P/\tau_N=3$.
Figure 17:
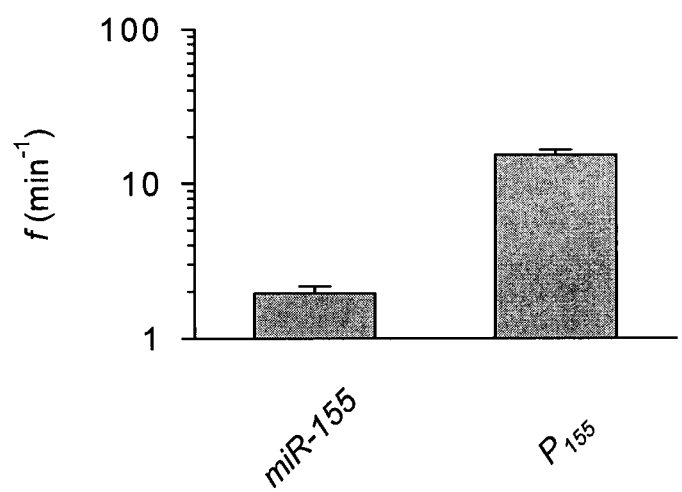
FIG. 17 shows translocation frequencies of miR-155 and $P_{155}$. Data was obtained from current traces recorded in 1 M KCl at +100 mV. The concentrations of both oligos were 100 nM.

Note S1. Precursor miRNAs (pre-miRNAs) are stem-loop RNAs of ~70 nucleotides bearing the 2 nucleotides 3'-overhang as a signature of RNase III-mediated cleavage (Lee, Y., Jeon, K., Lee, J. T., Kim, S., & Kim, V. N. MicroRNA maturation: stepwise processing and subcellular localization. *EMBO J* 21, 4663-4670 (2002)). It is not known whether the plasma total RNA extract contains pre-miRNAs. However, we have verified that the capture rate for a miR·P is very low if the signal tag in the probe is very short (FIG. 9, FIG. 16 and unpublished data). Therefore, we expected that, even though pre-miRNAs exist, the short overhang will prevent them from trapping in the nanopore.

Note S2. We also compared the time spent for analyzing miRNA via nanopore and qRT-PCR (in Supplementary Information). Our RT-PCR detection can test at most 16 samples at once, including triplicates for each sample with and without spike-in. PCR takes about 5-6 hours, including 1 hour PolyA reaction, 1 hour reverse transcription, 2.5 hours qPCR, plus 1 hour for sample addition. The nanopore method is label free, does not need amplification, and is selective for short nucleic acids fragments. But our current nanopore setup allows detecting one sample at once. The average recording time for miR-155 from human plasma sample was about 90 minutes, collecting ~100 events. Therefore, high through-put nanopore methods need developing. This is feasible because both the synthetic nanopore array [*Advanced Materials* 18, 3149-3153 (2006)] and the protein pore-synthetic pore hybridized system [*Nat. Nanotechnol.* 5, 874-877 (2010)] have been reported

TABLE 3

Sequences of studied miRNAs and their probes

| | |
|---|---|
| mir-155 | 5'-UUAAUGCUAAUCGUGAUAGGGG-3' (SEQ ID NO: 1) |
| $P_{nt}$ | 5'-CCCCTATCACGATTAGCATTAA-3' (SEQ ID NO: 2) |
| $P_{5'-C30}$ | 5'-$C_{30}$-CCCCTATCACGATTAGCATTAA-3' (SEQ ID NO: 3) |
| $P_{3'-C30}$ | 5'-CCCCTATCACGATTAGCATTAA-$C_{30}$-3' (SEQ ID NO: 4) |
| $P_{155}$ | 5'-$C_{30}$-CCCCTATCACGATTAGCATTAA-$C_{30}$-3' (SEQ ID NO: 5) |
| Let-7a | 5'-UGAGGUAGUAGGUUGU<u>AUA</u>GUU-3' (SEQ ID NO: 6) |
| $P_a$ | 5'-$C_{30}$-AACTATACAACCTACTACCTCA-$C_{30}$-3' (SEQ ID NO: 7) |
| Let-7b | 5'-UGAGGUAGUAGGUUGU<u>GUG</u>GUU-3' (SEQ ID NO: 8) |
| $P_b$ | 5'-$C_{30}$-AACCACACAACCTACTACCTCA-$C_{30}$-3' (SEQ ID NO: 9) |
| Let-7c | 5'-UGAGGUAGUAGGUUGU<u>AUG</u>GUU-3' (SEQ ID NO: 13) |
| $P_c$ | 5'-$C_{30}$-AACCATACAACCTACTACCTCA-$C_{30}$-3' (SEQ ID NO: 14) |
| miR-39 | 5'-UCACCGGGUGUAAAUCAGCUUG-3' (SEQ ID NO: 15) |
| $P_{39}$ | 5'-$C_{30}$-CAAGCTGATTTACACCCGGTGA-$C_{30}$-3' (SEQ ID NO: 16) |

TABLE 4

Conductance of signature events produced by the miR-155·P155 hybrid and spike-like short blocks by the translocation of miR-155 or P155 alone

| | Signature block (miR-155·$P_{155}$) | | | |
|---|---|---|---|---|
| | Level 1 | Level 2 | Level 3 | Short event |
| g (pS) | 203 | 585 | 110 | 227 |
| $g/g_0{}^a$ | 0.15 | 0.42 | 0.08 | 0.16 |

$^a g_0$, the conductance of unoccupied α-hemolysin pore. $g_0$ = 1380 pS at +100 mV in 1M KCl (pH8.0).

TABLE 5

Frequencies and occurrence rate constants of signature events detected with various probes

| Probe | $P_{nt}$ | $P_{5'-C30}$ | $P_{3'-C30}$ | $P_{155}$ |
|---|---|---|---|---|
| $f_{sig}$ (min$^{-1}$)$^a$ | 0.168 ± 0.042 (n = 5) | 0.408 ± 0.084 (n = 4) | 8.31 ± 2.1 (n = 5) | 11.9 ± 1.2 (n = 6) |
| $k_{on}$ (M$^{-1}$s$^{-1}$)$^b$ | 2.8 ± 0.6 × 10$^4$ | 6.8 ± 1.3 × 10$^4$ | 1.4 ± 0.3 × 10$^6$ | 2.0 ± 0.2 × 10$^6$ |

$^a$Frequencies in the presence of 100 nM miR-155 and the probe at +100 mV $^b$Occurrence rate constant from $f_{sig}$≈$k_{on}$ [miR-155], where [miR-155] = 100 nM

TABLE 6

Durations of signature events for fully-matched miRNA·probe hybrids and that with mismatches

| miRNA·Probe | let-7a·$P_a$ | let-7b·$P_a$ | let-7b·$P_b$ | let-7a·$P_b$ |
|---|---|---|---|---|
| $\tau_{sig}$ (ms) at +120 mV | 155 ± 28 (n = 7) | 48 ± 11 (n = 7) | 165 ± 47 (n = 6) | 24 ± 2 (n = 5) |
| p-value | <0.005 | | <0.005 | |
| miRNA·Probe | let-7a·$P_a$ | let-7c·$P_a$ | let-7c·$P_c$ | let-7a·$P_c$ |
| $\tau_{sig}$ (ms) at +100 mV | 303 ± 45 (n = 6) | 124 ± 39 (n = 4) | 343 ± 49 (n = 6) | 179 ± 38 (n = 4) |
| p-value | <0.005 | | <0.05 | |

TABLE 7

Areas under ROC curves (AUC) for separation of miRNAs with one nucleotide difference (let-7a and let-7c) and with two nucleotide difference (let-7a and let-7b)a

| | let-7a · $P_a$ | let-7b · $P_b$ | | let-7a · $P_a$ | let-7c · $P_c$ |
|---|---|---|---|---|---|
| let-7b · $P_a$ | 0.75 | n.a. | let-7c · $P_a$ | 0.73 | n.a. |
| let-7a · $P_b$ | n.a. | 0.83 | let-7a · $P_c$ | n.a. | 0.71 |

$^a$The receiver operating characteristic (ROC) curve is a plot of the true positive rate (sensitivity) against the false positive rate (1-selectivity) for the different possible cutoff points that separate the entire duration distribution into the positive and negative components. In the miRNA detection, the events for fully matched miRNA·probe hybrids were denoted as "positive", and that for mismatched hybrids as "negative". The separation accuracy was measured by the area under the ROC curve (AUC). An AUC of 1 represents a perfect separation; an area of 0.5 represents no separation ability. AUC was analyzed online using free software on the world wide web (internet address) rad.jhmi.edu/jeng/javarad/roc/JROCFITi.html.

TABLE 8

Areas under ROC curves (AUC) and optimal cutoff point (OCP) at various duration ratio and event number ratio a

| $\tau_P/\tau_N$ (s/s) [b] | 1/1 | 2/1 | 3/1 | 4/1 | 5/1 | 10/1 |
|---|---|---|---|---|---|---|
| AUC | 0.51 | 0.72 | 0.73 | 0.76 | 0.78 | 0.93 |
| OCP | n.a. | 1.33 | 1.74 | 1.88 | 1.98 | 2.18 |
| $N_P/N_N$ [c] | 200:800 | 200:400 | 200:200 | 200:150 | 200:100 | 200:50 |
| AUC | 0.83 | 0.81 | 0.76 | 0.76 | 0.79 | 0.78 |
| OCP | 1.88 | 1.88 | 1.85 | 1.79 | 1.81 | 1.97 | a: Both AUC and OCP were calculated from the ROC curves shown in FIG. 16A-B. OCP is a cutoff duration at the maximal value of Youden index. Youden index is defined as {sensitivity + selectivity − 1}, calculated from the ROC curve, and range between 0 and 1. A cutoff duration leading to complete separation of long and short duration distribution results in Youden index = 1, whereas complete overlap gives Youden index = 0. The cutoff duration value that returns the maximum of Youden index, i.e. "optimal" cutoff point (OCP) (Greiner et al., 2000 *Preventive Veterinary Medicine* 45, 23-41) gives the most accurate separation.
[b] $\tau_P/\tau_N$: The duration ratio of the "positive" and "negative" datasets. Each dataset contained 200 exponentially-distributed duration values. The dataset with a longer mean duration was denoted as "positive"; the shorter one as "negative".
[c] $N_P/N_N$: The event number ratio in the "positive" ($N_P$) versus the "negative" dataset. $\tau_P/\tau_N$ was 5 in this simulation.

TABLE 9

Levels of miR-155 and spiked-in miR-39 in human plasma samples detected by the nanopore sensor

| | Sample # | $f_{155}$ (min⁻¹) | $f_{39}$ (min⁻¹) | $f_{155}/f_{39}$ | Relative miR-155 level [a] |
|---|---|---|---|---|---|
| Normal | 1 | 0.67 ± 0.04 | 2.29 ± 0.34 | 0.292 | 1.22 |
| | 2 | 0.50 ± 0.13 | 2.62 ± 0.33 | 0.192 | 0.80 |
| | 3 | 0.62 ± 0.09 | 2.65 ± 0.25 | 0.236 | 0.99 |
| | 4 | 0.61 ± 0.12 | 2.35 ± 0.29 | 0.258 | 1.08 |
| | 5 | 0.68 ± 0.15 | 2.95 ± 0.20 | 0.230 | 0.97 |
| | 6 | 0.70 ± 0.06 | 3.14 ± 0.35 | 0.224 | 0.94 |
| | (Mean) [a] | | | 0.239 | 1 |
| Lung cancer | 7 | 1.63 ± 0.15 | 2.75 ± 0.44 | 0.593 | 2.49 |
| | 8 | 1.62 ± 0.14 | 2.58 ± 0.57 | 0.627 | 2.63 |
| | 9 | 1.71 ± 0.16 | 2.52 ± 0.21 | 0.675 | 2.83 |
| | 10 | 1.74 ± 0.18 | 2.76 ± 0.38 | 0.633 | 2.65 |
| | 11 | 1.69 ± 0.16 | 2.57 ± 0.25 | 0.658 | 2.76 |
| | 12 | 1.39 ± 0.11 | 2.74 ± 0.12 | 0.507 | 2.12 |
| | (Mean) | | | 0.615 | 2.57 |

[a] Relative miR-155 level was obtained by normalizing each sample's $f_{155}/f_{39}$ to the mean $f_{155}/f_{39}$ of the normal samples 1-6, which was 0.239 as highlighted in the table.

Example 3

Peptide-Guided Selective Detection of MicroRNAs

Rationales. Our long-term goal is developing the nanopore single molecule sensor for accurate detection of target miRNAs in the total RNA extraction from plasma or tissues. The RNA extraction contains numerous and complicated nucleic acids components, at least including miRNAs (both pre-mature and mature miRNAs), mRNAs, tRNAs, other RNAs. All components commonly carry negative charges. Thus, if the target miRNA can be trapped in the pore at an applied voltage, any other component may also be driven to interact with the nanopore, generating non-specific current signals that interfere with the recognition of signature events generated by the target miRNA/probe complex. Here we provide a robust strategy for which only the target miRNA/probe complex can be trapped in the pore, but any other nucleic acids components are prevented from interacting with the pore, therefore greatly improve the both selectivity and sensitivity. This strategy is called peptide-guided selective detection of miRNAs.

Methods. We designed a peptide-PNA (peptide nucleic acid) co-polymer as the probe, as shown in FIG. 18A. The PNA sequence (in "PNA" bracket in FIG. 18A) has a peptide backbone with side chain nucleobases that are complementary to the entire or partial sequence of the target miRNA ("miRNA (Let-7b, -7c)" in FIG. 18A bracket), and thus serves as the center domain for capturing the target miRNA in the solution. These sequences are provided as follows:

Probe

NH2-Tyr-Gly-Arg-Lys-Lys-Arg-Arg-Gln-Arg-Arg-Arg-AACCACACAA-COOH, where the entire probe has a peptide backbone (i.e. the AACCACACAA portion of the probe comprises a peptide backbone with the indicated AACCACACAA nucleobases); SEQ ID NO:17.

PNA (Center Domain) of Probe:

NH2-AACCACACAA-COOH, where the molecule comprises a peptide backbone with the indicated AACCACACAA nucleobases; (SEQ ID NO: 18).

HIV-TAT:

(SEQ ID NO: 19)
Tyr-Gly-Arg-Lys-Lys-Arg-Arg-Gln-Arg-Arg-Arg

As opposed to oligonucleotide probes, the reporter (or terminal extension) of the new probe is a peptide that carries a series of positively-charged amino acids ("Peptide reporter" in FIG. 18A bracket) and the center domain is a peptide nucleic acid comprising nucleotides that are complementary to the target nucleic acid. When there are a sufficient number of positively-charged amino acids in the reporter or terminal extension portion of the probe, the net charges of the miRNA/probe complex are still positive such that when the target miRNA binds to the PNA (peptide nucleic acid) domain of the probe the entire miRNA/probe complex forms a strong dipole molecule. We have engineered a nanopore with a negatively-charged residue ring at the trans opening of the pore (*S. aureus* alpha-hemolysin comprising a K131D mutation). The wild-type *S. aureus* alpha-hemolysin peptide sequence (National Center for Bioinformatics Accession NO. AAA26598.1); is:

(SEQ ID NO: 21)
ADSDINIKTGTTDIGSNTTVKTGDLVTYDKENGMHKKVFYSFIDDKNHN

KKLLVIRTKGTIAGQYRVYSEEGANKSGLAWPSAFKVQLQLPDNEVAQI

SDYYPRNSIDTKEYMSTLTYGFNGNVTGDDTGKIGGLIGANVSIGHTLK

YVQPDFKTILESPTDKKVGWKVIFNNMVNQNWGPYDRDSWNPVYGNQLF

MKTRNGSMKAADNFLDPNKASSLLSSGFSPDFATVITMDRKASKQQTNI

DVIYERVRDDYQLHWTSTNWKGTNTKDKWTDRSSERYKIDWEKEEMTN

The variant *S. aureus* K131D alpha-hemolysin peptide sequence is:

(SEQ ID NO: 22)
ADSDINIKTGTTDIGSNTTVKTGDLVTYDKENGMHKKVFYSFIDDKNHN

KKLLVIRTKGTIAGQYRVYSEEGANKSGLAWPSAFKVQLQLPDNEVAQI

SDYYPRNSIDTKEYMSTLTYGFNGNVTGDDTGDIGGLIGANVSIGHTLK

YVQPDFKTILESPTDKKVGWKVIFNNMVNQNWGPYDRDSWNPVYGNQLF

MKTRNGSMKAADNFLDPNKASSLLSSGFSPDFATVITMDRKASKQQTNI

DVIYERVRDDYQLHWTSTNWKGTNTKDKWTDRSSERYKIDWEKEEMTN

Therefore, the positively-charged peptide domain of the probe dipole will be both pushed by the positive voltage (cis grounded) and attracted by the negative ring at the trans opening, guiding the trapping of the miRNA/complex into the n-barrel of the pore. At the positive voltage, any other free nucleic acids components will be repulsed from entering the pore due to the negative charge carried. This significantly reduces signals by free RNA components, and most observed events are either due to the trapping of the miRNA/probe complex or the translocation of the probe. The use of peptide-PNA probe enables selective detection of the target miRNA.

Results. FIG. 18A shows the diagram of the miRNA/probe complex. The bracketed miRNA is target miRNA Let-7b. The bracketed probe P7b has a bracketed "Peptide Reporter" part and a bracketed "PNA" (peptide nucleic acid) part. The PNA is for capturing Let-7b, and the bracketed "Peptide reporter" is a positively-charged peptide corresponding the sequence of HIV-TAT, which contains +8e contributed by arginines and lysines. FIG. 18B shows events for translocation of the peptide-PNA probe, P7b. The characteristic events last for 3 ms and reduce the current to 10 pA at +180 mV. FIG. 18C shows no block events can be observed with free miRNA let-7b (without probe) in the solution at +180 mV.

FIG. 18D shows signature events for the trapping of the let-7b/P7b complex. These events characteristically last for 100 ms and reduce the current to 57 pA at +180 mV, completely different that for the probe. FIG. 18E shows that Let-7c, which has two different nucleotides from Let-7b, cannot bind to PNA of the probe P7b, therefore does not generate signature events as in FIG. 18C. Almost all observed events are due to the probe itself.

Figure 18F:
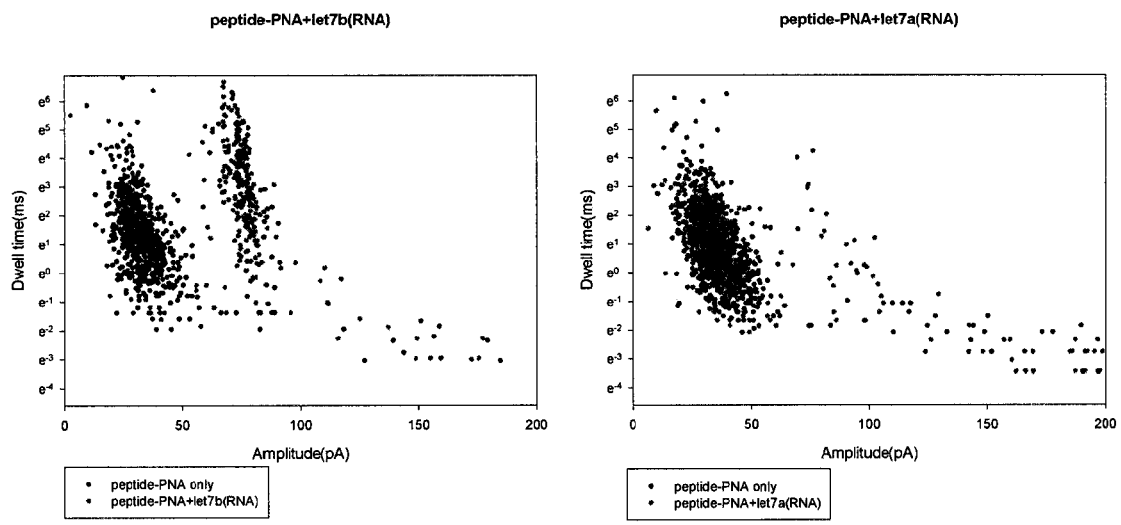
FIG. 18F compares the duration-amplitude property for P7b binding to Let-7b (fully match, two separate clusters without overlay) and Let-7c (2 mismatches, two clusters fully overlay).

FIG. 18F compares the duration-amplitude property for P7b binding to Let-7b (fully match, two separate clusters without overlay) and Let-7c (2 mismatches, two clusters fully overlay). This suggests an accuracy of almost 100% in differentiating sequence-similar miRNAs with two different nucleotides.

Utilization of signature events to understand various molecular processes in the nanopore for biosensing applications is also provided. In FIG. 19A, we observed a novel type of three-level current pattern when employing HP-C30 with a hairpin at the 3'-end of short strand. Its Level 1 and Level 2 are consistent with the unzipping of HP-C30 and translocation of the unzipped short strand from the nanocavity to the β-barrel. However, the duration of Level 1' was drastically prolonged by 80 folds to 15±1.9 ms, compared to the target without a hairpin. The prolonged Level 1' is in agreement with the unzipping of hairpin prior to threading in the β-barrel. As many DNA or RNA structures such as aptamers contain hairpins, we can use this system and the signature events to study these structures and study their binding interaction with their protein targets. In FIG. 19B, we also demonstrated a new multi-level current pattern when using SA-C30 attached with a streptavidin at the 3'-end of the short strand. Again, both the fully-blocked Level 1 and partially-blocked level 2 are consistent with the unzipping of SA-C30 and translocation of the unzipped short strand from the nanocavity to the β-barrel. The current stayed at Level 1' for minutes until it was forced to recover by a negative voltage. The long term Level 1' can be interpreted by that although the short strand of SA-C30 moves into the β-barrel after unzipping, its translocation is prevented by the attached large streptavidin. This result suggested the potential of using signature events for protein detection. In FIG. 19C, we demonstrated that the complex can be sequentially unzipped in the nanopore in two steps when using a short oligonucleotide to link two DNAs. The unzipping of the two DNAs can be clearly revealed by the two Level 2 states.

Conclusion. The peptide-PNA probe enables 1) selective detection of the target miRNA, 2) greatly enhanced accuracy in differentiating sequence-similar miRNAs.

While the invention has been described in connection with specific embodiments thereof, it will be understood that the inventive device is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

REFERENCES

1. Silvestri, G. A., Alberg, A. J., & Ravenel, J. The changing epidemiology of lung cancer with a focus on screening. *BMJ* 339, (2009).
2. Carthew, R. W. & Sontheimer, E. J. Origins and Mechanisms of miRNAs and siRNAs. *Cell* 136, 642-655 (2009).
3. Inui, M., Martello, G., & Piccolo, S., MicroRNA control of signal transduction. *Nat Rev Mol. Cell Biol* 11, 252-263 (2010).
4. Garzon, R., Calin, G. A., and Croce, C. M. MicroRNAs in cancer. 60, 167-179. 2009.
5. Ortholan, C., Puissegur, M. P., Ilie, M., Barbry, P., Mari, B., & Hofman, P. MicroRNAs and lung cancer: New oncogenes and tumor suppressors, new prognostic factors and potential therapeutic targets. *Curr. Med. Chem.* 16, 1047-1061 (2009).
6. Calin, G. A. & Croce, C. M. MicroRNA signatures in human cancers. *Nat Rev Cancer* 6, 857-866 (2006).
7. Mitchell, P. S., Parkin, R. K., Kroh, E. M., Fritz, B. R., Wyman, S. K., Pogosova-Agadjanyan, E. L., Peterson, A., Noteboom, J., O'Briant, K. C., Allen, A., Lin, D. W., Urban, N., Drescher, C. W., Knudsen, B. S., Stirewalt, D. L., Gentleman, R., Vessella, R. L., Nelson, P. S., Martin, D. B., & Tewari, M. Circulating microRNAs as stable blood-based markers for cancer detection. *Proc. Natl. Acad. Sci. U.S.A.* 105, 10513-10518 (2008).
8. Rabinowits, G., Gerãşel-Taylor, C., Day, J. M., Taylor, D. D., & Kloecker, G. H. Exosomal microRNA: A diagnostic marker for lung cancer. *Clin. Lung Cancer* 10, 42-46 (2009).
9. Kosaka, N., Iguchi, H., Yoshioka, Y., Takeshita, F., Matsuki, Y., & Ochiya, T. Secretory mechanisms and intercellular transfer of microRNAs in living cells. *J Biol Chem* (2010).
10. Rosell, R., Wei, J., & Taron, M. Circulating MicroRNA Signatures of Tumor-Derived Exosomes for Early Diagnosis of Non-Small-Cell Lung Cancer. *Clin. Lung Cancer* 10, 8-9 (2009).
11. Thomson, J. M., Parker, J., Perou, C. M., & Hammond, S. M. A custom microarray platform for analysis of microRNA gene expression. *Nat Methods* 1, 47-53 (2004).
12. Chen, C., Ridzon, D. A., Broomer, A. J., Zhou, Z., Lee, D. H., Nguyen, J. T., Barbisin, M., Xu, N. L., Mahuvakar, V. R., Andersen, M. R., Lao, K. Q., Livak, K. J., & Guegler, K. J. Real-time quantification of microRNAs by stem-loop RT-PCR. *Nucleic Acids Res.* 33, (2005).

13. Li, W. & Ruan, K. MicroRNA detection by microarray. *Anal. Bioanal. Chem.* 394, 1117-1124 (2009).
14. Hunt, E. A., Goulding, A. M., & Deo, S. K. Direct detection and quantification of microRNAs. *Anal. Biochem.* 387, 1-12 (2009).
15. Kloosterman, W. P., Wienholds, E., de Bruijn, E., Kauppinen, S., & Plasterk, R. H. In situ detection of miRNAs in animal embryos using LNA-modified oligonucleotide probes. *Nat Methods* 3, 27-29 (2006).
16. Neely, L. A., Patel, S., Garver, J., Gallo, M., Hackett, M., McLaughlin, S., Nadel, M., Harris, J., Gullans, S., & Rooke, J. A single-molecule method for the quantitation of microRNA gene expression. *Nat Methods* 3, 41-46 (2006).
17. Bayley, H. & Jayasinghe, L. Functional engineered channels and pores—(Review). *Molecular Membrane Biology* 21, 209-220 (2004).
18. Ma, L. & Cockroft, S. L. Biological nanopores for single-molecule biophysics. *Chembiochem* 11, 25-34 (2010).
19. Movileanu, L. Interrogating single proteins through nanopores: challenges and opportunities. *Trends Biotechnol.* 27, 333-341 (2009).
20. Bayley, H. Sequencing single molecules of DNA. *Current Opinion in Chemical Biology* 10, 628-637 (2006).
21. Branton, D., Deamer, D. W., Marziali, A., Bayley, H., Benner, S. A., Butler, T., DiVentra, M., Garaj, S., Hibbs, A., Huang, X., Jovanovich, S. B., Krstic, P. S., Lindsay, S., Ling, X. S., Mastrangelo, C. H., Meller, A., Oliver, J. S., Pershin, Y. V., Ramsey, J. M., Riehn, R., Soni, G. V., Tabard-Cossa, V., Wanunu, M., Wiggin, M., & Schloss, J. A. The potential and challenges of nanopore sequencing. *Nature Biotechnology* 26, 1146-1153 (2008).
22. Kasianowicz, J. J., Brandin, E., Branton, D., & Deamer, D. W. Characterization of individual polynucleotide molecules using a membrane channel. *Proc. Natl. Acad. Sci. U.S.A.* 93, 13770-13773 (1996).
23. Akeson, M., Branton, D., Kasianowicz, J. J., Brandin, E., & Deamer, D. W. Microsecond time-scale discrimination among polycytidylic acid, polyadenylic acid, and polyuridylic acid as homopolymers or as segments within single RNA molecules. *Biophys. J* 77, 3227-3233 (1999).
24. Meller, A., Nivon, L., & Branton, D. Voltage-driven DNA translocations through a nanopore. *Phys Rev Lett* 86, 3435-3438 (2001).
25. Deamer, D. W. & Branton, D. Characterization of nucleic acids by nanopore analysis. *Acc. Chem. Res.* 35, 817-825 (2002).
26. Nakane, J., Akeson, M., & Marziali, A. Nanopore sensors for nucleic acid analysis. *J Phys Condens Matter* 15, (2003).
27. Mitchell, N. & Howorka, S. Chemical tags facilitate the sensing of individual DNA strands with nanopores. *Angew. Chem. Int. Ed.* 47, 5565-5568 (2008).
28. Rabinowits, G., GerÃ§el-Taylor, C., Day, J. M., Taylor, D. D., & Kloecker, G. H. Exosomal microRNA: A diagnostic marker for lung cancer. *Clin. Lung Cancer* 10, 42-46 (2009).
29. Rosell, R., Wei, J., & Taron, M. Circulating microRNA signatures of tumor-derived exosomes for early diagnosis of non-small-cell lung cancer. *Clin. Lung Cancer* 10, 8-9 (2009).
30. Meller, A., Nivon, L., Brandin, E., Golovchenko, J., & Branton, D. Rapid nanopore discrimination between single polynucleotide molecules. *Proc. Natl. Acad. Sci. U.S.A.* 97, 1079-1084 (2000).
31. Sauer-Budge, A. F., Nyamwanda, J. A., Lubensky, D. K., & Branton, D. Unzipping kinetics of double-stranded DNA in a nanopore. *Phys Rev Lett* 90, (2003).
32. Mathés, J., Visram, H., Viasnoff, V., Rabin, Y., & Meller, A. Nanopore unzipping of individual DNA hairpin molecules. *Biophys. J* 87, 3205-3212 (2004).
33. Maglia, G., Restrepo, M. R., Mikhailova, E., & Bayley, H. Enhanced translocation of single DNA molecules through +/−-hemolysin nanopores by manipulation of internal charge. *Proc. Natl. Acad. Sci. U.S.A.* 105, 19720-19725 (2008).
34. Shim, J. W., Tan, Q., & Gu, L. Q. Single-molecule detection of folding and unfolding of a single G-quadruplex aptamer in a nanopore nanocavity. *Nucleic Acids Res.* 37, 972-982 (2009).
35. Butler, T. Z., Gundlach, J. H., & Troll, M. A. Determination of RNA orientation during translocation through a biological nanopore. *Biophys. J.* 90, 190-199 (2006).
36. Kasianowicz, J. J., Brandin, E., Branton, D., & Deamer, D. W. Characterization of individual polynucleotide molecules using a membrane channel. *Proc. Natl. Acad. Sci. U.S.A.* 93, 13770-13773 (1996).
37. Mathés, J., Aksimentiev, A., Nelson, D. R., Schulten, K., & Meller, A. Orientation discrimination of single-stranded DNA inside the Î±-hemolysin membrane channel. *Proc. Natl. Acad. Sci. U.S.A.* 102, 12377-12382 (2005).
38. Purnell, R. F., Mehta, K. K., & Schmidt, J. J. Nucleotide identification and orientation discrimination of DNA homopolymers immobilized in a protein nanopore. *Nano Lett.* 8, 3029-3034 (2008).
39. Wanunu, M., Morrison, W., Rabin, Y., Grosberg, A. Y., & Meller, A. Electrostatic focusing of unlabelled DNA into nanoscale pores using a salt gradient. *Nature Nanotechnology* 5, 160-165 (2010).
40. Cho, W. C. Role of miRNAs in lung cancer. *Expert Rev Mol. Diagn.* 9, 773-776 (2009).
41. Landi, M. T., Zhao, Y., Rotunno, M., Koshiol, J., Liu, H., Bergen, A. W., Rubagotti, M., Goldstein, A. M., Linnoila, I., Marincola, F. M., Tucker, M. A., Bertazzi, P. A., Pesatori, A. C., Caporaso, N. E., McShane, L. M., & Wang, E. MicroRNA expression differentiates histology and predicts survival of lung cancer. *Clin. Cancer Res* 16, 430-441 (2010).
42. Patnaik, S. K., Kannisto, E., Knudsen, S., & Yendamuri, S. Evaluation of microRNA expression profiles that may predict recurrence of localized stage I non-small cell lung cancer after surgical resection. *Cancer Res* 70, 36-45 (2010).
43. Yanaihara, N., Caplen, N., Bowman, E., Seike, M., Kumamoto, K., Yi, M., Stephens, R. M., Okamoto, A., Yokota, J., Tanaka, T., Calin, G. A., Liu, C. G., Croce, C. M., & Harris, C. C. Unique microRNA molecular profiles in lung cancer diagnosis and prognosis. *Cancer Cell* 9, 189-198 (2006).
44. Shi, R. & Chiang, V. L. Facile means for quantifying microRNA expression by real-time PCR. *BioTechniques* 39, 519-524 (2005).
45. Kim, M. J., Wanunu, M., Bell, D. C., & Meller, A. Rapid fabrication of uniformly sized nanopores and nanopore arrays for parallel DNA analysis. *Advanced Materials* 18, 3149-3153 (2006).

What is claimed is:

1. A method of detecting an oligonucleotide in a sample with a nanopore system, comprising the steps of:
   a) mixing a sample suspected of comprising a target oligonucleotide and a probe, said probe comprising a central domain with a complementary sequence to said target oligonucleotide and a terminal extension tagged to at least one of a 3' terminal or a 5' terminal of the central domain, to produce a sample mixture wherein said central domain of said probe hybridizes to said target oligonucleotide,
   b) applying a voltage to said sample mixture in a cis compartment of a dual chamber nanopore system sufficient to drive translocation of said hybridized probe and target oligonucleotide through a nanopore of said system by an unzipping process, and
   c) analyzing an electrical current pattern in said nanopore system over time,
   wherein a presence of said target oligonucleotide in said sample is indicated by at least one signature electrical current block that is distinct from a background electrical current block that occurs with said sample alone or said probe alone.

2. The method of claim 1, wherein said signature electrical current block comprises at least one of: i) a current block of different duration than a background current block; ii) a different number of distinct current blockade levels than a background current block; iii) a different order of occurrence of current blockade levels than a background current block; iv) a blockade level having a different current amplitude than a background current block; v) a current amplitude of each blockade level different than a current amplitude of a background current block; or any combination of (i), (ii), (iii), (iv), or (v).

3. The method of claim 1, wherein at least one terminal extension is a charged polypeptide or an oligonucleotide.

4. The method of claim 1, wherein said terminal extension comprises a charged polypeptide containing at least two positively charged amino acids, at least two aromatic amino acid residues, or at least two positively charged amino acids and at least two aromatic amino acid residues.

5. The method of claim 4, wherein said charged polypeptide provides for a net positive charge when said probe is hybridized to said target oligonucleotide.

6. The method of claim 1, wherein said nanopore comprises a negatively charged residue ring at a trans opening of the nanopore.

7. The method of claim 1, wherein said nanopore comprises an alpha-hemolysin variant comprising a K131D, K131E, or K131H amino acid substitution.

8. The method of claim 1, wherein steps (a) and (b) or step (b) are performed at a pH value of less than 7.

9. The method of claim 1, wherein said target oligonucleotide is a DNA molecule or an RNA molecule.

10. The method of claim 9, wherein said RNA molecule is an miRNA or a fragment thereof, and wherein said fragment comprises at least 15 nucleotides of said RNA molecule.

11. The method of claim 1, wherein a frequency of said signature electrical current block is used to quantitate an amount of said target oligonucleotide in said sample.

12. The method of claim 1, wherein a non-target oligonucleotide is spiked into said sample and a frequency of electrical current blocks attributable to said non-target oligonucleotide is used to normalize a frequency of the signature electrical current block.

13. The method of claim 1, wherein said central domain of said probe comprises at least 15 nucleotides or nucleobases that are complementary to the target oligonucleotide.

14. A method for detecting two or more distinct target oligonucleotides that differ by at least one nucleotide in a sample with a nanopore system, comprising the steps of:
   a) mixing a sample suspected of comprising said distinct target oligonucleotides and a probe, said probe comprising a central domain with a fully or partially complementary sequence to said target oligonucleotides and a terminal extension tagged to at least one of a 3' terminal or a 5' terminal of the central domain, to produce a sample mixture wherein said central domain of said probe hybridizes to said target oligonucleotides,
   b) applying a voltage to said sample mixture in a cis compartment of a dual chamber nanopore system sufficient to drive translocation of hybridized probe and target oligonucleotides through a nanopore of said system by an unzipping process, and
   c) analyzing an electrical current pattern in said nanopore system over time, wherein a presence of two or more distinct target oligonucleotides in said sample is indicated by two or more distinct signature electrical current blocks.

15. The method of claim 14, wherein said two or more distinct signature electrical current blocks comprise at least one of: i) different signature electrical current block durations (τsig); ii) a different number of distinct current blockade levels; iii) a different order of occurrence of current blockade levels; iv) a different current amplitude; v) a different current amplitude of each blockade level; or any combination of (i), (ii), (iii), (iv), or (v).

16. The method of claim 14, wherein said target oligonucleotides are DNA molecules or RNA molecules.

17. The method of claim 16, wherein said RNA molecules are miRNAs or fragments thereof, and wherein said fragments comprise at least 15 nucleotides of said RNA molecules.

18. The method of claim 14, wherein the terminal extension is a charged polypeptide or an oligonucleotide.

19. The method of claim 18, wherein the charged polypeptide comprises at least two positively charged amino acids at least two aromatic amino acid residues, or at least two positively charged amino acids and at least two aromatic amino acid residues.

20. The method of claim 19, wherein said charged polypeptide provides for a net positive charge when said probe is hybridized to said target oligonucleotides.

21. The method of claim 19, wherein said nanopore comprises a negatively charged residue ring at a trans opening of the nanopore.

22. The method of claim 19, wherein said nanopore comprises an alpha-hemolysin variant comprising a K131D, a K131E, or a K131H amino acid substitution.

23. The method of claim 14, wherein said central domain comprises at least 15 nucleotides or nucleobases that are complementary to the target oligonucleotides.

24. A kit comprising, (a) a probe comprising a central domain with a fully or partially complementary sequence to a target oligonucleotide and a terminal extension tagged to at least one of a 3' terminal or a 5' terminal of the central domain, wherein said probe comprises at least one terminal extension that is a charged polypeptide, and wherein said central domain of said probe can hybridize to the target oligonucleotide; and (b) a nanopore.

25. The kit of claim 24, wherein said central domain comprises a peptide nucleic acid probe.

26. The kit of claim 24, wherein the charged polypeptide comprises at least two positively charged amino acids, at least two aromatic amino acid residues, or at least two positively charged amino acids and at least two aromatic amino acid residues.

27. The kit of claim 26, wherein said charged polypeptide provides for a net positive charge when said probe is hybridized to the target oligonucleotide.

28. The kit of claim 24, wherein said nanopore comprises a negatively charged residue ring at a trans opening of the nanopore.

29. The kit of claim 24, wherein said nanopore comprises an alpha-hemolysin variant comprising a K131D, a K131E, or a K131H amino acid substitution.

* * * * *

SEQUENCE LISTING

<160> NUMBER OF SEQ ID NOS: 22

<210> SEQ ID NO 1
<211> LENGTH: 22
<212> TYPE: RNA
<213> ORGANISM: Homo sapiens

<400> SEQUENCE: 1
uuaaugcuaa ucgugauagg gg                                              22

<210> SEQ ID NO 2
<211> LENGTH: 22
<212> TYPE: DNA
<213> ORGANISM: Artificial
<220> FEATURE:
<223> OTHER INFORMATION: synthetic

<400> SEQUENCE: 2
cccctatcac gattagcatt aa                                              22

<210> SEQ ID NO 3
<211> LENGTH: 52
<212> TYPE: DNA
<213> ORGANISM: Artificial
<220> FEATURE:
<223> OTHER INFORMATION: synthetic

<400> SEQUENCE: 3
cccccccccc cccccccccc cccccccccc cccctatcac gattagcatt aa             52

<210> SEQ ID NO 4
<211> LENGTH: 52
<212> TYPE: DNA
<213> ORGANISM: Artificial
<220> FEATURE:
<223> OTHER INFORMATION: synthetic

<400> SEQUENCE: 4
cccctatcac gattagcatt aacccccccc cccccccccc cccccccccc cc             52

<210> SEQ ID NO 5
<211> LENGTH: 82
<212> TYPE: DNA
<213> ORGANISM: Artificial
<220> FEATURE:
<223> OTHER INFORMATION: synthetic

<400> SEQUENCE: 5
cccccccccc cccccccccc cccccccccc cccctatcac gattagcatt aacccccccc     60
cccccccccc cccccccccc cc                                              82

<210> SEQ ID NO 6
<211> LENGTH: 22
<212> TYPE: RNA
<213> ORGANISM: Homo sapiens

<400> SEQUENCE: 6
ugagguagua gguuguauag uu                                              22

<210> SEQ ID NO 7
<211> LENGTH: 82
<212> TYPE: DNA
<213> ORGANISM: Artificial
<220> FEATURE:
<223> OTHER INFORMATION: synthetic

<400> SEQUENCE: 7
cccccccccc cccccccccc cccccccccc aactatacaa cctactacct caccccccccc       60 cccccccccc cccccccccc cc       82

<210> SEQ ID NO 8
<211> LENGTH: 22
<212> TYPE: RNA
<213> ORGANISM: Homo sapiens

<400> SEQUENCE: 8
ugagguagua gguugugugg uu       22

<210> SEQ ID NO 9
<211> LENGTH: 82
<212> TYPE: DNA
<213> ORGANISM: Artificial
<220> FEATURE:
<223> OTHER INFORMATION: synthetic

<400> SEQUENCE: 9
cccccccccc cccccccccc cccccccccc aaccacacaa cctactacct caccccccccc       60 cccccccccc cccccccccc cc       82

<210> SEQ ID NO 10
<211> LENGTH: 49
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (49)..(49)
<223> OTHER INFORMATION: n is a, c, g, or t

<400> SEQUENCE: 10
gcgagcacag aattaatacg actcactata ggttttttttt tttttttvn       49

<210> SEQ ID NO 11
<211> LENGTH: 23
<212> TYPE: DNA
<213> ORGANISM: Artificial
<220> FEATURE:
<223> OTHER INFORMATION: synthetic

<400> SEQUENCE: 11
ttaatgctaa tcgtgatagg ggt       23

<210> SEQ ID NO 12
<211> LENGTH: 22
<212> TYPE: DNA
<213> ORGANISM: Artificial
<220> FEATURE:
<223> OTHER INFORMATION: synthetic

<400> SEQUENCE: 12
gcgagcacag aattaatacg ac       22

<210> SEQ ID NO 13
<211> LENGTH: 22
<212> TYPE: RNA
<213> ORGANISM: Homo sapiens

<400> SEQUENCE: 13
ugagguagua gguuguaugg uu       22

-continued

<210> SEQ ID NO 14
<211> LENGTH: 82
<212> TYPE: DNA
<213> ORGANISM: Artificial
<220> FEATURE:
<223> OTHER INFORMATION: synthetic

<400> SEQUENCE: 14
cccccccccc cccccccccc cccccccccc aaccatacaa cctactacct cacccccccc    60
cccccccccc cccccccccc cc    82

<210> SEQ ID NO 15
<211> LENGTH: 22
<212> TYPE: RNA
<213> ORGANISM: Homo sapiens

<400> SEQUENCE: 15
ucaccgggug uaaaucagcu ug    22

<210> SEQ ID NO 16
<211> LENGTH: 82
<212> TYPE: DNA
<213> ORGANISM: Artificial
<220> FEATURE:
<223> OTHER INFORMATION: synthetic

<400> SEQUENCE: 16
cccccccccc cccccccccc cccccccccc caagctgatt tacacccggt gacccccccc    60
cccccccccc cccccccccc cc    82

<210> SEQ ID NO 17
<211> LENGTH: 21
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: peptide nucleic acid adenine residue
<220> FEATURE:
<221> NAME/KEY: MISC_FEATURE
<222> LOCATION: (13)..(13)
<223> OTHER INFORMATION: peptide nucleic acid adenine residue
<220> FEATURE:
<221> NAME/KEY: MISC_FEATURE
<222> LOCATION: (14)..(14)
<223> OTHER INFORMATION: peptide nucleic acid cytosine residue
<220> FEATURE:
<221> NAME/KEY: MISC_FEATURE
<222> LOCATION: (15)..(15)
<223> OTHER INFORMATION: peptide nucleic acid cytosine residue
<220> FEATURE:
<221> NAME/KEY: MISC_FEATURE
<222> LOCATION: (16)..(16)
<223> OTHER INFORMATION: peptide nucleic acid adenine residue
<220> FEATURE:
<221> NAME/KEY: MISC_FEATURE
<222> LOCATION: (17)..(17)
<223> OTHER INFORMATION: peptide nucleic acid cytosine residue
<220> FEATURE:
<221> NAME/KEY: MISC_FEATURE
<222> LOCATION: (18)..(18)
<223> OTHER INFORMATION: peptide nucleic acid adenine residue
<220> FEATURE:
<221> NAME/KEY: MISC_FEATURE
<222> LOCATION: (19)..(19)
<223> OTHER INFORMATION: peptide nucleic acid cytosine residue -continued

```
<220> FEATURE:
<221> NAME/KEY: MISC_FEATURE
<222> LOCATION: (20)..(20)
<223> OTHER INFORMATION: peptide nucleic acid adenine residue
<220> FEATURE:
<221> NAME/KEY: MISC_FEATURE
<222> LOCATION: (21)..(21)
<223> OTHER INFORMATION: peptide nucleic acid adenine residue

<400> SEQUENCE: 17

Tyr Gly Arg Lys Lys Arg Arg Gln Arg Arg Xaa Xaa Xaa Xaa Xaa
1               5                   10                  15

Xaa Xaa Xaa Xaa Xaa
            20

<210> SEQ ID NO 18
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: peptide nucleic acid adenine residue
<220> FEATURE:
<221> NAME/KEY: MISC_FEATURE
<222> LOCATION: (2)..(2)
<223> OTHER INFORMATION: peptide nucleic acid adenine residue
<220> FEATURE:
<221> NAME/KEY: MISC_FEATURE
<222> LOCATION: (3)..(3)
<223> OTHER INFORMATION: peptide nucleic acid cytosine residue
<220> FEATURE:
<221> NAME/KEY: MISC_FEATURE
<222> LOCATION: (4)..(4)
<223> OTHER INFORMATION: peptide nucleic acid cytosine residue
<220> FEATURE:
<221> NAME/KEY: MISC_FEATURE
<222> LOCATION: (5)..(5)
<223> OTHER INFORMATION: peptide nucleic acid adenine residue
<220> FEATURE:
<221> NAME/KEY: MISC_FEATURE
<222> LOCATION: (6)..(6)
<223> OTHER INFORMATION: peptide nucleic acid cytosine residue
<220> FEATURE:
<221> NAME/KEY: MISC_FEATURE
<222> LOCATION: (7)..(7)
<223> OTHER INFORMATION: peptide nucleic acid adenine residue
<220> FEATURE:
<221> NAME/KEY: MISC_FEATURE
<222> LOCATION: (8)..(8)
<223> OTHER INFORMATION: peptide nucleic acid cytosine residue
<220> FEATURE:
<221> NAME/KEY: MISC_FEATURE
<222> LOCATION: (9)..(9)
<223> OTHER INFORMATION: peptide nucleic acid adenine residue
<220> FEATURE:
<221> NAME/KEY: MISC_FEATURE
<222> LOCATION: (10)..(10)
<223> OTHER INFORMATION: peptide nucleic acid adenine residue

<400> SEQUENCE: 18

Xaa Xaa Xaa Xaa Xaa Xaa Xaa Xaa Xaa Xaa
1               5                   10

<210> SEQ ID NO 19
<211> LENGTH: 11
<212> TYPE: PRT
<213> ORGANISM: Human immunodeficiency virus
```

<400> SEQUENCE: 19

Tyr Gly Arg Lys Lys Arg Arg Gln Arg Arg Arg
1               5                   10

<210> SEQ ID NO 20
<211> LENGTH: 882
<212> TYPE: DNA
<213> ORGANISM: Staphylococcus aureus

<400> SEQUENCE: 20

```
gcagattctg atattaatat taaaaccggt actacagata ttggaagcaa tactacagta     60
aaaacaggtg atttagtcac ttatgataaa gaaaatggca tgcacaaaaa agtattttat    120
agttttatcg atgataaaaa tcacaataaa aaactgctag ttattagaac gaaaggtacc    180
attgctggtc aatatagagt ttatagcgaa gaaggtgcta acaaaagtgg tttagcctgg    240
ccttcagcct ttaaggtaca gttgcaacta cctgataatg aagtagctca aatatctgat    300
tactatccaa gaaattcgat tgatacaaaa gagtatatga gtactttaac ttatggattc    360
aacggtaatg ttactggtga tgatacagga aaaattggcg gccttattgg tgcaaatgtt    420
tcgattggtc atacactgaa atatgttcaa cctgatttca aaacaatttt agagagccca    480
actgataaaa aagtaggctg gaaagtgata tttaacaata tggtgaatca aaattgggga    540
ccatatgata gagattcttg gaacccggta tatggcaatc aacttttcat gaaaactaga    600
aatggttcta tgaaagcagc agataacttc cttgatccta acaaagcaag ttctctatta    660
tcttcagggt tttcaccaga cttcgctaca gttattacta tggatagaaa agcatccaaa    720
caacaaacaa atatagatgt aatatacgaa cgagttcgtg atgattacca attgcattgg    780
acttcaacaa attggaaagg taccaatact aaagataaat ggacagatcg ttcttcagaa    840
agatataaaa tcgattggga aaagaagaa atgacaaatt aa                         882
```

<210> SEQ ID NO 21
<211> LENGTH: 293
<212> TYPE: PRT
<213> ORGANISM: Staphylococcus aureus

<400> SEQUENCE: 21

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

```
Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
            210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
            275                 280                 285

Glu Glu Met Thr Asn
            290

<210> SEQ ID NO 22
<211> LENGTH: 293
<212> TYPE: PRT
<213> ORGANISM: Staphylococcus aureus

<400> SEQUENCE: 22

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
            115                 120                 125

Thr Gly Asp Ile Gly Gly Leu Ile Gly Ala Asn Val Ser Ile Gly His
            130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
            210                 215                 220
```

-continued

```
Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
            245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```